US006852737B2

(12) United States Patent
Bonifacio et al.

(10) Patent No.: US 6,852,737 B2
(45) Date of Patent: Feb. 8, 2005

(54) CRUDE AND CRYSTALLINE FORMS OF LERCANIDIPINE HYDROCHLORIDE

(75) Inventors: Fausto Bonifacio, Latina (IT); Francesco Campana, Rocca Priora (IT); Gianluca De Iasi, Aprilia (IT); Amedeo Leonardi, Milan (IT)

(73) Assignee: Recordati Ireland Limited, Ringaskiddy (IR)

( * ) Notice: Subject to any disclaimer, the term of this patent is extended or adjusted under 35 U.S.C. 154(b) by 128 days.

(21) Appl. No.: 10/214,386

(22) Filed: Aug. 6, 2002

(65) Prior Publication Data

US 2003/0083355 A1 May 1, 2003

Related U.S. Application Data

(60) Provisional application No. 60/367,789, filed on Mar. 26, 2002.

(30) Foreign Application Priority Data

Aug. 6, 2001 (IT) .................................. MI2001 A 001727
Aug. 6, 2001 (IT) .................................. MI2001 A 001726

(51) Int. Cl.$^7$ .................. A61K 31/4418; C07D 213/46
(52) U.S. Cl. ..................... 514/321; 546/356; 514/321
(58) Field of Search ............................ 546/321; 514/356

(56) References Cited

U.S. PATENT DOCUMENTS

| 4,285,955 | A |   | 8/1981  | Wehinger et al. |
|-----------|---|---|---------|-----------------|
| 4,705,797 | A |   | 11/1987 | Nardi et al.    |
| 4,968,832 | A |   | 11/1990 | Nardi et al.    |
| 5,248,699 | A |   | 9/1993  | Sysko et al.    |
| 5,696,139 | A |   | 12/1997 | Leonardi et al. |
| 5,767,136 | A | * | 6/1998  | Sartani et al. ............. 514/356 |
| 5,912,351 | A |   | 6/1999  | Leonardi et al. |
| 2001/0002404 | A1 |   | 5/2001  | Webb et al.    |
| 2001/0029257 | A1 |   | 10/2001 | Murdock et al. |
| 2001/0044584 | A1 |   | 11/2001 | Kensey         |
| 2001/0056095 | A1 |   | 12/2001 | Mylari         |
| 2002/0010208 | A1 |   | 1/2002  | Shashoua et al. |
| 2002/0015713 | A1 |   | 2/2002  | Murdock et al. |
| 2002/0032149 | A1 |   | 3/2002  | Kensey         |
| 2002/0042405 | A1 |   | 4/2002  | Schuh          |
| 2002/0061835 | A1 |   | 5/2002  | Kensey         |
| 2002/0068740 | A1 |   | 6/2002  | Mylari         |
| 2002/0099046 | A1 |   | 7/2002  | Scott          |
| 2002/0137755 | A1 |   | 9/2002  | Bilodeau et al. |

FOREIGN PATENT DOCUMENTS

| EP | 0 153 016    | 5/1990  |
|----|--------------|---------|
| WO | WO 96/35668  | 11/1996 |
| WO | WO 97/03669  | 2/1997  |

OTHER PUBLICATIONS

McClellan and Jarvis, (2000) "Lercanidipine: A Review of its Use in Hypertension", Adis Drug Evaluation' 60:1 123–1140.*

Leonardi et al. (1998) "Asymmetric N–(3,3–diphenylpropyl)aminoalkyl esters of 4–aryl–2,6–dimethyl–1,4–dihydropyridine,–3,5–dicarboxylic acids with antihypertensive activity", Eur. J. Med. Chem., 33:399–420.

McClellan and Jarvis, (2000) "Lercanidipine: A Review of its Use in Hypertension", Adis Drug Evaluation, 60:1123–1140.

(1987) REC 15/2375, Drugs of the Future, 12:1113–1115.

* cited by examiner

Primary Examiner—Joseph K. McKane
Assistant Examiner—Janet L Coppins
(74) Attorney, Agent, or Firm—Darby & Darby

(57) ABSTRACT

The invention describes novel lercanidipine crude Forms (A) and (B), novel lercanidipine hydrochloride crystalline Forms (I) and (II) obtained from said crude Forms, pharmaceutical, antihypertensive compositions containing as active agent at least one of the lercanidipine hydrochloride crystalline Forms (I) and (II) and methods of use thereof.

18 Claims, 19 Drawing Sheets

SOLUBILITY IN WATER-ETHANOL

FORM II DRUG SUBSTANCE IR SPECTRUM

CRUDE AND CRYSTALLINE FORMS OF LERCANIDIPINE HYDROCHLORIDE

RELATED APPLICATIONS

The present application claims priority under 35 U.S.C. 119 (e) of U.S. provisional application 60/367,789, filed Mar. 26, 2002 and priority under 35 U.S.C. 119 (a)–(d) of Italian patent applications MI 2001A 001726 and MI 2001A 001727, both filed Aug. 6, 2001. Each of the aforementioned applications is hereby incorporated herein by reference in its entirety.

FIELD OF THE INVENTION

The invention is directed to novel crude forms and crystalline forms of lercanidipine hydrochloride, and to processes for the preparation of these forms. Pharmaceutical compositions comprising the novel crystalline forms are also contemplated.

BACKGROUND OF THE INVENTION

Lercanidipine (methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate) is a highly lipophilic dihydropyridine calcium antagonist with long duration of action and high vascular selectivity. Its mechanism of antihypertensive activity is attributed to a direct relaxant effect on vascular smooth muscle, which lowers total peripheral resistance. The recommended starting dose of lercanidipine as monotherapy is 10 mg daily by oral route, with a drug titration as necessary to 20 mg daily. Lercanidipine is rapidly absorbed following oral administration with peak plasma levels occurring 2–3 hours following dosing. Elimination is essentially via the hepatic route.

By virtue of its high lipophilicity and high membrane coefficient, lercanidipine combines a short plasma half life with a long duration of action. In fact, the preferential distribution of the drug into membranes of smooth muscle cells results in membrane-controlled pharmacokinetics characterized by a prolonged pharmacological effect. In comparison to other calcium antagonists, lercanidipine is characterized by gradual onset and long-lasting duration of action despite decreasing plasma levels. In vitro studies show that isolated rat aorta response to high $K^+$ may be attenuated by lercanidipine, even after the drug has been removed from the environment of the aortic tissue for 6 hours.

Lercanidipine is commercially available from Recordati S.p.A. (Milan, Italy) and has been described along with methods for making it and resolving it into individual enantiomers in U.S. Pat. Nos. 4,705,797; 5,767,136; 4,968,832; 5,912,351; and 5,696,139. A process for preparing lercanidipine described in U.S. Pat. No. 4,705,797 involves the following scheme:

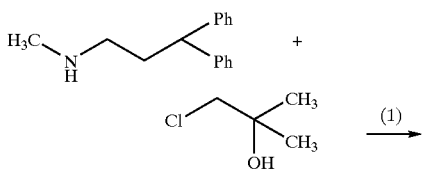

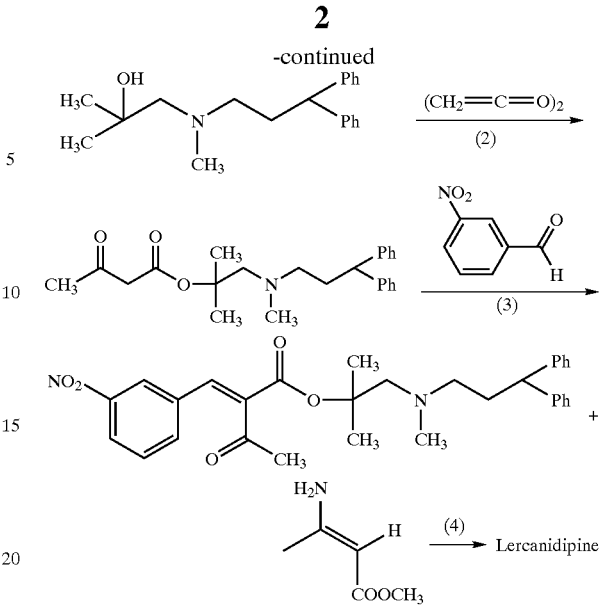

(1) xylene at reflux; (2) toluene, 85° C.; (3) HCl + CHCl$_3$; 0° C.;
(4) HO—CH(CH$_3$)$_2$ at reflux (1): xylene at reflux; (2): toluene, 85° C.; (3) HCl+CHCl$_3$; 0° C.; (4) HO—CH(CH$_3$)$_2$ at reflux Crude lercanidipine is an oily residue that must be purified by flash chromatography using chloroform, containing increasing amounts of acetone, as the eluant. The solvent is then evaporated to dryness and remaining residue is dissolved in methanol adding a small excess of hydrochloric acid in ethanol. After evaporation of the solvent, the hemihydrated hydrochloride salt is prepared by treatment with diluted hydrochloric acid in the presence of sodium chloride.

A major disadvantage of the process of preparing lercanidipine, as it is described in U.S. Pat. No. 4,705,797, is that the disclosed cyclization reaction generates several by-products, which results in a lower yield for the desired product. Moreover, the purification and isolation of lercanidipine from the reaction mixture is quite complex, since it requires numerous treatments with different solvents. Finally, the purification and isolation steps are difficult to perform on an industrial scale because of the necessity of purifying the product by column chromatography.

U.S. Pat. No. 5,912,351 describes a simpler process for the preparation of lercanidipine hydrochloride. It involves reaction of 1,4-dihydro-2,6-dimethyl-5-methoxycarbonyl-4-(3-nitrophenyl)pyridine-3-carboxylic acid with thionyl chloride in dichloromethane and dimethylformamide at a temperature between −4 and +1° C. and subsequent esterification of the obtained acid chloride with 2, N-dimethyl-N-(3,3-diphenylpropyl)-1-amino-2-propyl alcohol at a temperature between −10 and 0° C. The process yields lercanidipine hydrochloride in an anhydrous non-hygroscopic crystalline form, and avoids the formation of unwanted by-products and the subsequent purification on chromatography columns.

However, the isolation of lercanidipine hydrochloride in crystalline form is again quite complex. After evaporating the solvent from the reaction mixture and dissolving the residue thus obtained in ethyl acetate, the solution is washed first with brine, then washed further five times with a 10% solution of sodium carbonate, five times with 1N hydrochloric acid, and eventually once again with brine.

Therefore, there is a need in the art for a process for the preparation of lercanidipine hydrochloride in crystalline form which avoids one more of the disadvantages of the currently used processes.

In addition, it was observed that lercanidipine, as produced by the second-described process above, displayed batch-to-batch variability despite careful process control and even observation of the melting point believed to be characteristic of the solid product obtained by the process of Example 3 of U.S. Pat. No. 5,767,136 of 186–188° C. This variability was manifest in seemingly unpredictably appearing (and disappearing) differences in one or more of product appearance (e.g., color), melting point and solubility. This raised issues as to whether assurances of purity and/or reproducibility can be made (e.g., to regulatory authorities) that the product is always the same.

Further research by the present inventors revealed batch-to-batch differences in bioavailability in animals, and differences in crystal size. In the course of researching the causes of the variability problem, the inventors surprisingly discovered novel lercanidipine hydrochloride polymorphs. They also discovered more suitable processes for the preparation and isolation of crystalline lercanidipine hydrochloride products from the reaction mixture. It was surprisingly determined that lercanidipine hydrochloride shows polymorphic features and crystallizes into different crystalline forms depending on the process followed and on the solvents used. Furthermore, the isolation of each of individual crystalline polymorphs has become possible, thus decreasing the possibility of batch to batch variability of lercanidipine, which the present inventors determined was due to mixtures of different solid forms being present by the same batch and to such mixtures of different composition having melting points within the same narrow range as the individual forms. As a result, more reproducible batches of lercanidipine more suitable for large scale manufacture and quality control were needed.

SUMMARY OF THE INVENTION

The present invention provides novel crude forms and crystalline forms of lercanidipine hydrochloride and processes for making them.

In one embodiment, the invention provides novel crude lercanidipine hydrochloride Form (A), which has a melting point of about 150–152° C. (DSC peak) and comprises about 3–4% (w/w) ethyl acetate.

In another embodiment, the invention provides novel crude lercanidipine hydrochloride Form (B) which has a melting point of about 131–135° C. (DSC peak) and comprises about 0.3–0.7% (w/w) ethyl acetate.

Methods are provided for the independent syntheses of crude lercanidipine hydrochloride Form (A) and crude lercanidipine hydrochloride Form (B), making possible to obtain each crude form in isolated form.

In a further embodiment, isolated lercanidipine hydrochloride crystalline Form (I) is provided which has the following X-ray diffraction pattern, at wavelength Kα wherein distances between peaks (D in Å), relative intensity ratios (I/Io) ratios, and angles of significant peaks (2θ) are:

| D (Å) | Relative intensity (I/Io) | 2 θ angle |
|---|---|---|
| 16.3 | 83 | 5.4 |
| 6.2 | 47 | 14.2 |
| 4.78 | 29 | 18.6 |
| 4.10 | 63 | 21.7 |
| 4.06 | 36 | 21.9 |
| 3.90 | 100 | 22.8 |

The lercanidipine hydrochloride crystalline Form (I) has a melting point of about 197–201° C., when said melting point is determined as DSC peak.

In an alternative embodiment, isolated lercanidipine hydrochloride crystalline Form (II) is provided, which has the following X-ray diffraction pattern, at wavelength Kα, as shown wherein distances, (I/Io) ratios, and 2 θ angles of significant peaks are:

| D (Å) | Relative intensity (I/Io) | 2 θ angle |
|---|---|---|
| 9.3 | 35 | 9.5 |
| 6.0 | 45 | 14.7 |
| 5.49 | 65 | 16.1 |
| 4.65 | 52 | 19.1 |
| 4.27 | 74 | 20.8 |
| 3.81 | 41 | 23.4 |
| 3.77 | 100 | 23.6 |
| 3.58 | 44 | 24.8 |
| 3.54 | 29 | 25.2 |

The lercanidipine hydrochloride crystalline Form (II) has a melting point of about 207–211° C., when said melting point is determined as DSC peak.

The present invention thus permits obtaining mixtures of Form I and Form II having a predetermined and reproducible content of each form, and optionally, also other forms of lercanidipine, such as amorphous.

Also provided are methods of syntheses in which each of isolated lercanidipine hydrochloride crystalline Form (I) and Form (II) may be obtained, independently, from the starting material of lercanidipine hydrochloride crude Form (A) or crude Form (B).

Also provided are pharmaceutical compositions comprising (1) crystalline lercanidipine hydrochloride and optionally other forms of lercanidipine, such as amorphous, wherein the crystalline lercanidipine hydrochloride is selected from the group consisting of lercanidipine hydrochloride crystalline Form (I), lercanidipine hydrochloride crystalline Form (II), and combinations thereof comprising a predetermined content of each crystalline form, and (2) at least one component selected from the group consisting of a pharmaceutically acceptable carrier or diluent, a flavorant, a sweetener, a preservative, a dye, a binder, a suspending agent, a dispersing agent, a colorant, a disintegrant, an excipient, a lubricant, a plasticizer, and an edible oil.

In certain embodiments the aforementioned pharmaceutical compositions are provided as a dosage form comprising lercanidipine hydrochloride crystalline Form (I) or Form (II) or a combination thereof having a predetermined formulation of each crystalline Form.

In further embodiments, the invention also provides for methods of treating a subject with arterial hypertension, the method comprising administering a therapeutically effective amount of lercanidipine hydrochloride crystalline Form (I), lercanidipine hydrochloride crystalline Form (II), or combinations thereof comprising a predetermined content of each form to a subject in need of such treatment.

In other embodiments, a method of treating or preventing atherosclerotic lesions in arteries of a subject is provided, the method comprising administering a therapeutically effective amount of lercanidipine hydrochloride crystalline Form (I), lercanidipine hydrochloride crystalline Form (II), or combinations thereof comprising a predetermined amount of each form, to a subject in need of such treatment. In preferred aspect, a subject in need of treatment is a mammal. Most preferably the subject in need of treatment is a human.

These and other aspects of the present invention will be apparent to those of ordinary skill in the art in light of the present description, claims and figures.

DETAILED DESCRIPTION OF THE INVENTION

Figure 1:
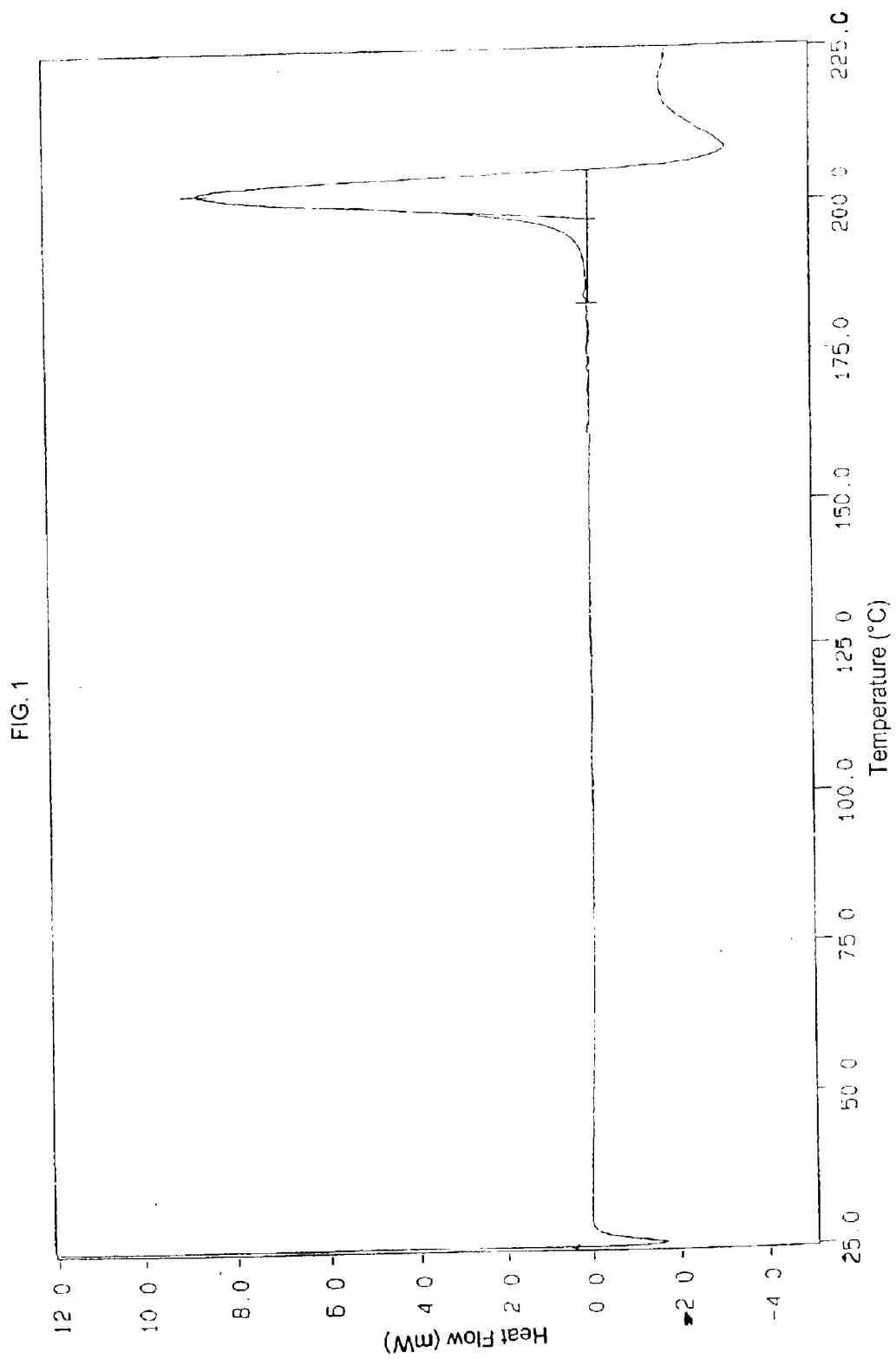
FIG. 1 is a graph of DSC analysis carried out on crystalline Form (I), according to the working conditions described in Example 12. The ordinate indicates heat flow in mW and the abscissa temperature in ° C.

The present invention discloses novel crude forms and crystalline forms of lercanidipine hydrochloride and processes for making them. Applicants have determined that lercanidipine hydrochloride exhibits polymorphism and crystallizes in different forms depending on the process followed and on the solvents used, especially for crystallization. Additionally, the various novel forms have distinct chemical and physical properties and bioavailability profiles in animals, including man, as discussed herein.

The novel methods for preparation of crude of lercanidipine hydrochloride are suitable for highly reproducible commercial scale production of reproducible solid compositions of lercanidipine hydrochloride. The methods advantageously produce novel crude Forms (A) and (B) of lercanidipine hydrochloride which also exhibit characteristics desirable for industrial applications. Crude Forms (A) and (B), e.g., exhibit higher solubility and faster drying rates compared to other crude forms of lercanidipine hydrochloride that have previously been reported. Crude Forms (A) and (B) further allow simplified crystallization procedures to be used for production of novel isolated crystalline forms of lercanidipine hydrochloride.

The novel isolated crystalline forms of lercanidipine hydrochloride of the present invention can be obtained from lercanidipine hydrochloride crude Forms (A) and (B) and are termed lercanidipine hydrochloride crystalline Form (I) and Form (II). Either of isolated Form (I) or isolated Form (II) may be reproducibly obtained from the (A) and (B) intermediates by varying the crystallization conditions as described below. Forms (I) and (II) may also be obtained using other starting materials. Both of Forms (I) and (II) may be obtained using, for example, crude lercanidipine Form (C) as starting material, as described herein. Form (II) may also be obtained using Form (I) as starting material, as described herein.

Both lercanidipine hydrochloride crystalline Forms (I) and (II) exhibit good stability. Form (I) is characterized by a paler yellow color, smaller crystal size, higher solubility in aqueous media (all compared to Form (II)), and a melting point (DSC peak) within the rage of about 197° C. to about 201° C., more specifically, about 198.7° C., and the X-ray diffraction pattern set forth, supra.

Form (II) is characterized by a more pronounced yellow color, larger crystal size, slightly lower solubility in aqueous media (all compared to Form (I)), and a melting point (DSC peak) within the range of about 207–211° C., more specifically about 209.3° C.

Both Form (I) and Form (II) are stable. Form II exhibited higher bioavailability in the dog, and was also non equivalent to form I in man, showing a higher plasma concentration (AUCo-t) and a delayed time of maximum concentration (tmax), compared to Form (I).

Methods known in the art for producing crystalline lercanidipine hydrochloride were inconsistent in producing lercanidipine hydrochloride with predictable physical and chemical characteristics. Hence, prior art methods had the undesirable property of producing lercanidipine hydrochloride that varied, e.g., in physico-chemical properties, from batch to batch, even among batches produced by the same process and under the same conditions. The present inventors have discovered that the source of inconsistency exhibited by the prior art methods of producing lercanidipine hydrochloride is the presence of varying and unpredictable amounts of crystalline lercanidipine hydrochloride Form (II). In contrast to prior art methods of producing lercanidipine hydrochloride, the invention provides the novel crystalline Forms (I) and (II) that represent crystalline forms of lercanidipine hydrochloride of a purity and uniformity that has not been obtained with previously achieved solid forms of lercanidipine hydrochloride.

The purity and uniformity of Forms (I) and (II) allow for increased ease in production of lercanidipine dosage forms, due to, e.g., more precisely defined physico-chemical characteristics, such as, for example, increased uniformity of particle size following micronization and more reproducible solubility. Forms (I) and (II) also provide dosage forms with more precisely defined pharmacological characteristics, e.g., bioavailability, compared to previously achieved dosage forms that varied from batch-to-batch in their physico-chemical characteristics.

In a human study in man, where the plasma levels of lercanidipine were assessed after administration of a single dose of either lercanidipine hydrochloride Form (I) or (II), Form (I) had shorter time in obtaining the maximum concentration in plasma, relative to Form (II). Hence, Form (I) is more suited for immediate release formulations and dosage forms. From the same study, Form (II) showed a higher bioavailability, relative to Form (I), and is thus suited for use in controlled release formulations and dosage forms. Accordingly, the availability of pure Forms (I) and (II) provides for the ability to blend the two polymorphs into dosage forms with novel controlled characteristics, e.g., a dosage form with both a rapid onset and sustained biological action.

As used herein, the term "crude form" refers to precipitated solid forms comprising crystals of a compound that have not been washed and/or recrystallized to remove impurities (including but not limited to solvent) that may be present and which lack, e.g., melting point and x-ray spectra characteristic of crystalline forms. In the present specification, the crude forms are referred to as Forms (A) and (B) of lercanidipine hydrochloride.

As used herein, the term "crystalline form" refers to crystals of a compound that have been washed and recrystallized to remove impurities, or having melting point and x-ray spectra characteristic of crystalline forms. In the present invention, unless specifically stated otherwise, the term crystalline forms refers to Forms (I) and (II) of lercanidipine hydrochloride. These crystalline forms have an HPLC purity ≧99.5% and residual solvents content of <3000 ppm. Additional lercanidipine hydrochloride crystalline forms, i.e., lercanidipine hydrochloride crystalline Forms (III) and (IV) are described in Italian patent application no. MI 2001A 001727, filed Aug. 6, 2001, and in co-pending U.S. application Ser. No. 10/214,385 of Leonardi et al., for "NOVEL SOLVATE AND CRYSTALLINE FORMS OF LERCANIDIPINE HYDROCHLORIDE", filed Aug. 6, 2002.

As used herein, the term "polymorphism" refers to a property of a compound to crystallize in two or more forms with distinct structures. The different crystalline forms can be detected directly by crystallographic techniques or indirectly by assessment of differences in physical and/or chemical properties associated with each particular polymorph.

As used herein, a "subject in need of treatment" is a mammalian (e.g., human) subject suffering from or at risk of developing the particular condition to be treated, e.g., essential hypertension, secondary hypertension, isolated systolic hypertension, coronary heart disease (e.g., chronic stable angina, myocardial infarction), congestive heart failure. A subject in need of treatment for arterial hypertension may be identified using methods well known in the art such as, for example, by direct measurement of blood pressure using, for example, a manual sphygmomanometer, automatic/electronic devices or ambulatory blood pressure monitoring.

As used herein, a "therapeutically effective amount" of an agent is an amount sufficient to ameliorate at least one symptom associated with a pathological, abnormal or otherwise undesirable condition, an amount sufficient to prevent or lessen the probability that such a condition will occur or re-occur, or an amount sufficient to delay worsening of such a condition. An amount sufficient to lower blood pressure to values lower than 140/90 is recommended. Recent World Health Organization guidelines recommended a diastolic blood pressure lower than 85 mm Hg. and a systolic blood pressure lower than 130 mm Hg. in younger patients and in diabetic patients. Treatment of other pathologies, such as heart failure or artherosclerois is also specifically contemplated as per, e.g., U.S. Pat. Nos. 5,696,139 and 5,767,136.

The present invention contemplates any method that may be used to produce the novel crude forms of lercanidipine hydrochloride described herein. These forms have different physico-chemical properties, e.g., melting points (which can be determined by DSC analysis), than the crude form of lercanidipine hydrochloride produced by other known methods, e.g., by the method described in U.S. Pat. No. 5,912,351; termed Form (C). Form (A) has a melting point of about 150° C. to about 152° C. (DSC peak), Form (B) has a melting point of about 131° C. to about 135° C. (DSC peak), and Form (C) has a melting point of about 186° C. to about 192° C. (DSC peak). Additionally, thermogravimetric studies show that Form (A) comprises 3–4% residual ethyl acetate and Form (B) comprises 0.3–0.7% residual ethyl acetate, by weight. Comparatively, the residual solvent present in Form (C) has been determined to be 0–0.1%.

Aspects of the invention are directed to processes for the preparation of lercanidipine hydrochloride, each resulting in a different crude form of the product. The first two steps in producing either crude form are identical and are:

(a) reacting 2,6-dimethyl-5-methoxycarbonyl-4-(3-nitrophenyl)-1,4-dihydropyridine-3-carboxylic acid (prepared as described in German patent DE 2847 237) with thionyl chloride or oxalyl chloride in a mixture of an aprotic dipolar solvent and of an aprotic polar solvent to yield a chloride compound, and (b) in-situ reaction of the chloride obtained from the above step with 2, N-dimethyl-N-(3,3-diphenylpropyl)-1-amino-2-propyl alcohol, at a temperature preferably between −5 and +5° C., in a mixture of an aprotic dipolar solvent and of an aprotic polar solvent.

In a preferred embodiment, the mixture of an aprotic dipolar solvent and of an aprotic polar solvent is ethyl acetate and dimethylformamide used at a ratio of 4:1.

After the in-situ reaction, the lercanidipine hydrochloride is isolated and recovered from the mixture. The method of isolation used determines the crude form of lercanidipine hydrochloride obtained. Following the protocol below (α protocol) yields Form (A):

i) washing the mixture of step (b), preferably with water, ii) removing water from the reaction mixture of step i), preferably by azeotropic distillation under vacuum at 200–300 mmHg at a temperature below about 60° C. (preferably at 40–50° C.);

iii) concentrating the mixture of step ii) preferably to about ⅓ of the initial volume at the same temperature and pressure as in step (ii), adding fresh solvent (e.g., ethyl acetate) preferably to obtain the initial volume, thus obtaining a suspension with a water content, as determined according to Karl Fischer (U.S. Pharmacopoeia 25, Method 921) preferably between 0.10 and 0.15%;

iv) cooling the suspension of step iii) preferably to 0–5° C.;

v) filtering the solid of step iv);

vi) re-suspending the solid of step v) preferably in ethyl acetate and stirring preferably at 60–65° C. for about 1 hour; and vii) cooling to 5–10° C., filtering and drying the obtained solid (e.g., in an oven at about 70° C.).

The second process (β protocol; used to prepare Form (B)) is performed using the following steps:

i') washing the mixture of step (b) preferably with water, ii') removing the water from step i') preferably by azeotropically refluxing the product of step i') with a Dean Stark apparatus until a water content of about 2%, measured according to Karl Fischer, is obtained;

iii') concentrating the mixture of step ii') to preferably ¾ of the initial volume and adding fresh solvent (ethyl acetate) to the mixture preferably until (1) the initial volume is achieved and (2) a water content, measured according to Karl Fischer, between 0.9 and 1.1% is obtained;

iv') cooling the solution of step iii') preferably to 0–5° C. to obtain a solid;

v') filtering the solid of step iv');

vi') re-suspending the solid of step v') preferably in ethyl acetate and stirring at preferably 60–65° C. for about 1 hour; and vii') cooling the suspension of step vi') preferably to 5–10° C., filtering and drying the solid obtained, preferably in an oven at about 70° C.

The temperature of step vii') should be carefully controlled at 5–10° C. to maximize yield.

These novel crude forms of lercanidipine hydrochloride present the advantage of higher solubility and faster drying rate compared to Form (C) and make a simplified further crystallization process possible (which can advantageously be used to prepare Form (I) or Form (II)). Compared to the crude form produced by the method of U.S. Pat. No. 5,912,351, these forms permit use of less solvent to recrystallize the compound. This also increases yield by reducing loss of compound. Additionally, the methods used to produce these crude forms are more adaptable to use in a large scale setting and commercial setting.

It has been surprisingly found that each of crude lercanidipine hydrochloride Form (A) and Form (B), when undergoing different purification treatments, result in two novel and different crystalline forms of lercanidipine hydrochloride. Studies indicate that these novel crystalline forms have different physical and chemical properties. DSC analysis of crystalline Form (I) indicates that it has a melting peak of about 197° C. to about 201° C., specifically about 198.7° C. DSC analysis of crystalline Form (II) indicates that it has a melting peak of about 207° C. to about 211° C., specifically about 209.3° C.

One purification process (γ process), that leads to formation of one of the novel crystalline forms (Form (I)) comprises the following steps:

Process for Making Form (I)

d) adding isopropanol to crude lercanidipine hydrochloride (Form (A) or Form (B)) and heating under reflux with stirring to produce a solution (if the solution is not clear, it should be filtered hot);

e) cooling the solution of step d) preferably to a temperature between 30 and 40° C. and stirring for a period of time preferably between 12 and 48 hours to produce a solid; and f) filtering the solid obtained from step e), washing the solid with isopropanol, re-filtering the solid, and drying the solid (e.g., in an oven) at preferably 70° C. for a period of time preferably between 12–48 hours.

Crude Form (C) may be also be used as starting material in step d). In such case, however, there is the risk of decreased yield of product because the solution should be filtered hot, resulting in the increased loss of lercanidipine hydrochloride in step d). In step e), crystallization is considered complete when the content of the solution is ≦2% lercanidipine HCl. Other alcohols may also be used as the solvent in step d). An alternatively preferred solvent is a $C_1$–$C_5$ alcohol containing a maximum of 5% water, e.g., anhydrous ethanol. Crystalline Form (I) may be added in step (e) as seeds to further promote crystal formation.

Alternative Process for Making Form (I)

The present application also contemplates an alternative method of producing lercanidipine hydrochloride having crystalline Form (I) which comprises the steps of:

d') adding ethanol to crude lercanidipine hydrochloride, preferably at a weight/volume ratio of lercanidipine hydrochloride solvent of 1:4 to 1:6, most preferably 1:4, refluxing under stirring in order to obtain a solution (if the solution is not clear it should preferably be filtered hot), cooling under stirring, preferably to 20° C., and adding crystalline seeds of Form (I);

e') cooling the seeded mixture of step d'), preferably to a temperature between 10 and 15° C., and stirring at this temperature for a period of time preferably between 24 and 96 hours to form a solid; and f') filtering and drying the solid of step e'), it preferably in an oven at preferably 70° C. to obtain lercanidipine hydrochloride Form (I).

In step e'), crystallization is considered complete when the content of the solution is ≦2% lercanidipine hydrochloride. Crystalline seeds of Form (I) may also be added to steps e') to further promote crystal formation.

Process for Making Form (II)

The second purification process (δ process), which yields crystalline Form (II), comprises the steps of:

d") adding acetonitrile to crude lercanidipine hydrochloride (Form (A) or Form (B)) and heating the mixture under reflux and stirring, e") cooling of the mixture of step d") to room temperature and stirring preferably for 24 hours to form a solid, f") filtering the solid obtained from step e") and drying it preferably in an oven.

In step e"), crystallization is considered complete when the content of the solution is ≦2% lercanidipine HCl.

The present application also contemplates two additional methods for producing Form (II).

First Alternative Process for Making Form (II)

The first alternative method comprises the steps of:

d''') adding isopropanol or ethanol, preferably ethanol, with a water content preferably between 5 to 10% by weight to lercanidipine hydrochloride, refluxing with stirring to produce a solution;

e''') cooling the mixture to a temperature preferably between 20 and 40° C. and stirring for a period preferably between 24 and 96 hours to form a solid;

f''') filtering the solid and drying (e.g., in an oven) at preferably 70° C. for 12–18 hours to produce lercanidipine hydrochloride Form (II).

In step e'''), crystallization is considered complete when the content of the solution is ≦2% lercanidipine HCl.

Second Alternative Method for Making Form II

The second alternative method of obtaining the Form (II) polymorph comprises the steps of:

d'''') dissolving crude lercanidipine hydrochloride or its crystalline Form (I) in a protic polar or an aprotic dipolar solvents preferably containing up to 50% by weight of water at a temperature preferably between 20 and 70° C. to produce a solution;

e'''') stirring the solution of step d'''') at a temperature preferably between 20 and 25° C. to produce a solid;

f'''') filtering the solid of step e'''') and drying (e.g., in an oven) at preferably 70° C. for preferably 12–18 hours.

The second alternative method may optionally comprise the step of adding up to 60% water to the solution of step d'''') prior to step e''''). The second alternative method may further comprise irradiating with ultrasound and/or adding preferably authentic crystalline seeds of Form (II) to step e''''). In step e''''), crystallization is considered complete when the content of the solution is ≦2% lercanidipine HCl. In a preferred embodiment, the protic polar solvent is an alcohol solvent such as, but not limited to, methanol, ethanol, n-propanol, isopropanol. In another preferred embodiment, the aprotic dipolar solvent is N-methylpyrrolidone.

The preferred process for preparing Form (I) is the γ process and the preferred process for preparing Form (II) is the δ process. Applicants have determined that Form (I) can be quantitatively obtained by use of $C_1$–$C_5$ anhydrous alcohol (preferably anhydrous ethanol or isopropanol) or $C_1$–$C_5$ alcohol containing up to 5% water under controlled conditions d'–f'). In fact, the foregoing processes, especially the γ and δ processes can be used to produce the desired polymorph reproducibly and consistently.

In addition to differences in melting point, the two crystalline forms exhibit differences in x-ray structure, solubility, and bioavailability. Solubility studies show that Form (I) is more soluble than Form (II) in water, ethanol, and mixtures thereof (See Tables 2 & 3). Bioavailability studies in dogs and humans indicate that Form (II) is more bioavailable than Form (I). The study in humans also indicates, however, that Form (I) has a shorter time to maximum concentration attainable and is thus suitable for use in immediate release formulations and dosage forms. Finally, x-ray diffraction studies show that these two forms have different diffraction patterns (see FIGS. 11 and 12 and Example 20). Form I has a smaller crystal and hence particle size before micronization and so is easier and faster to process than Form II, which presents with larger crystals.

The present application further discloses pharmaceutical formulations and unit dosage forms that comprise one of the isolated polymorphs of the present invention or a mixture thereof of predetermined polymorph content.

The present invention is also directed to a method of treating a subject with hypertension (e.g., essential hypertension, secondary hypertension or isolated systolic hypertension), coronary heart disease (e.g., chronic stable angina, myocardial infarction) or congestive heart failure the method comprising administering a therapeutically effective amount of isolated lercanidipine hydrochloride crystalline Form (I), lercanidipine hydrochloride crystalline Form (II), or combinations thereof of predetermined polymorph content (optionally with other form of lercanidipine, such as amorphous form) to a subject in need of such treatment.

The invention also contemplates a method of treating and preventing atherosclerotic lesions in arteries of a subject, the method comprising administering a therapeutically effective amount of isolated lercanidipine hydrochloride crystalline Form (I), isolated lercanidipine hydrochloride crystalline Form (II), or combinations thereof to a subject in need of such treatment.

Pharmaceutical Compositions

The compounds and polymorphs of the present invention may be formulated into a pharmaceutical composition. The pharmaceutical composition may also include optional additives, such as a pharmaceutically acceptable carrier or diluent, a flavorant, a sweetener, a preservative, a dye, a binder, a suspending agent, a dispersing agent, a colorant, a disintegrant, an excipient, a film forming agent, a lubricant, a plasticizer, an edible oil or any combination of two or more of the foregoing.

Both crystalline forms can undergo micronization, using any method known in the art. The average size of particle produced by this method are preferably D(50%)2–8 μm, D(90%)<15 μm.

Suitable pharmaceutically acceptable carriers or diluents include, but are not limited to, ethanol; water; glycerol; propylene glycol, aloe vera gel; allantoin; glycerin; vitamin A and E oils; mineral oil; PPG2 myristyl propionate; magnesium carbonate; potassium phosphate; vegetable oil; animal oil; and solketal.

Suitable binders include, but are not limited to, starch; gelatin; natural sugars, such as glucose, sucrose and lactose; corn sweeteners; natural and synthetic gums, such as acacia, tragacanth, vegetable gum, and sodium alginate; carboxymethylcellulose; hydroxypropylmethylcellulose; polyethylene glycol; povidone; waxes; and the like.

Suitable disintegrants include, but are not limited to, starch, e.g., corn starch, methyl cellulose, agar, bentonite, xanthan gum, sodium starch glycolate, crosspovidone and the like.

Suitable lubricants include, but are not limited to, sodium oleate, sodium stearate, sodium stearyl fumarate, magnesium stearate, sodium benzoate, sodium acetate, sodium chloride and the like.

A suitable suspending agent is, but is not limited to, bentonite, ethoxylated isostearyl alcohols, polyoxyethylene sorbitol and sorbitan esters, microcrystalline cellulose, aluminum metahydroxide, agar-agar and tragacanth, or mixtures of two or more of these substances, and the like.

Suitable dispersing and suspending agents include, but are not limited to, synthetic and natural gums, such as vegetable gum, tragacanth, acacia, alginate, dextran, sodium carboxymethylcellulose, methylcellulose, polyvinylpyrrolidone and gelatin.

Suitable film forming agents include, but are not limited to, hydroxypropylmethylcellulose, ethylcellulose and polymethacrylates.

Suitable plasticizers include, but are not limited to, polyethylene glycols of different molecular weights (e.g., 200–8000 Da) and propylene glycol.

Suitable colorants include, but are not limited to, ferric oxide(s), titanium dioxide and natural and synthetic lakes.

Suitable edible oils include, but are not limited to, cottonseed oil, sesame oil, coconut oil and peanut oil.

Examples of additional additives include, but are not limited to, sorbitol, talc, stearic acid, dicalcium phosphate and polydextrose.

Unit Dosage Forms

The pharmaceutical composition may be formulated as unit dosage forms, such as tablets, pills, capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any delivery of active ingredients that results in systemic availability of them can be used. Preferably the unit dosage form is an oral dosage form, most preferably a solid oral dosage form, therefore the preferred dosage forms are tablets, pills, caplets and capsules. Parenteral preparations (e.g., injectable preparations and preparations for powder jet systems) also are preferred.

Solid unit dosage forms may be prepared by mixing an active agent of the present invention with a pharmaceutically acceptable carrier and any other desired additives as described above. The mixture is typically mixed until a homogeneous mixture of the active agents of the present invention and the carrier and any other desired additives is formed, i.e., until the active agent is dispersed evenly throughout the composition. In this case, the compositions can be formed as dry or moist granules.

Dosage forms with predetermined amounts of lercanidipine hydrochloride may be formulated starting with compositions with known quantities of lercanidipine hydrochloride using methods well known in the art. In a preferred embodiment a dosage form is obtained by mixing compositions comprising known quantities of crystalline lercanidipine hydrochloride, e.g., Form (I) or (II), optionally including non-crystalline lercanidipine hydrochloride. Further preferred is where a dosage form with predetermined amounts of crystalline lercanidipine hydrochloride is formulated by mixing compositions comprising essentially pure crystalline lercanidipine hydrochloride are mixed to form dosage forms comprising a predetermined ratio of crystalline Forms (I) and (II).

Dosage forms can be formulated as, for example, "immediate release" dosage forms. "Immediate release" dosage forms are typically formulated as tablets that release at least 70%–90% of the active ingredient within 30–60 min when tested in a drug dissolution test, e.g., U.S. Pharmacopeia standard <711>. In a preferred embodiment, immediate dosage forms release at 75% of active ingredient in 45 min.

Dosage forms can also be formulated as, for example, "controlled release" dosage forms. "Controlled," "sustained," "extended" or "time release" dosage forms are equivalent terms that describe the type of active agent delivery that occurs when the active agent is released from a delivery vehicle at an ascertainable and manipulatable rate over a period of time, which is generally on the order of minutes, hours or days, typically ranging from about sixty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract. Typical parameters for dissolution test of controlled release forms are found in U.S. Pharmacopeia standard <724>.

Dosage forms can also be formulated to deliver active agent in multiphasic stages whereby a first fraction of an active ingredient is released at a first rate and at least a second fractions of active ingredient is released at a second rate. In a preferred embodiment, a dosage form can be formulated to deliver active agent in a biphasic manner, comprising a first "immediate release phase", wherein a fraction of active ingredient is delivered at a rate set forth above for immediate release dosage forms, and a second "controlled release phase," wherein the remainder of the active ingredient is released in a controlled release manner, as set forth above for controlled release dosage forms.

Tablets or pills can be coated or otherwise compounded to form a unit dosage form which has delayed and/or prolonged action, such as time release and controlled release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents, include, but are not limited to, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For liquid dosage forms, the active substances or their physiologically acceptable salts are brought into solution, suspension or emulsion, optionally with the usually employed substances such as solubilizers, emulsifiers or other auxiliaries. Solvents for the active combinations and the corresponding physiologically acceptable salts, can include water, physiological salt solutions or alcohols, e.g. ethanol, propane-diol or glycerol. Additionally, sugar solutions such as glucose or mannitol solutions may be used. A mixture of the various solvents mentioned may further be used in the present invention.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and controlled release of the active agents of the present invention.

Pharmaceutical compositions and unit dosage forms of the present invention for administration parenterally, and in particular by injection, typically include a pharmaceutically acceptable carrier, as described above. A preferred liquid carrier is vegetable oil. Injection may be, for example, intravenous, intrathecal, intramuscular, intraruminal, intratracheal, or subcutaneous.

The active agent also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The polymorphs of the present invention also may be coupled with soluble polymers as targetable drug carriers. Such polymers include, but are not limited to, polyvinylpyrrolidone, pyran copolymer, polyhydroxypropylmethacryl-amidephenol, polyhydroxyethylaspartamidephenol, and polyethyleneoxideopolylysine substituted with palmitoyl residues.

Administration

The pharmaceutical composition or unit dosage forms of the present invention may be administered by a variety of routes such as intravenous, intratracheal, subcutaneous, oral, mucosal parenteral, buccal, sublingual, ophthalmic, pulmonary, transmucosal, transdermal, and intramuscular. Unit dosage forms also can be administered in intranasal form via topical use of suitable intranasal vehicles, or via transdermal routes, using those forms of transdermal skin patches known to those of ordinary skill in the art. Oral administration is preferred.

The pharmaceutical composition or unit dosage forms of the present invention may be administered to an animal, preferably a human being, in need of antihypertensive treatment. The pharmaceutical composition or unit dosage form of the present invention may be administered according to a dosage and administration regimen defined by routine testing in light of the guidelines given above in order to obtain optimal antihypertensive activity and a decreased in blood pressure while minimizing toxicity or side-effects for a particular patient. However, such fine turning of the therapeutic regimen is routine in light of the guidelines given herein.

The dosage of the composition containing polymorphs or mixtures of the present invention may vary according to a variety of factors such as underlying disease state, the individual's condition, weight, sex and age and the mode of administration. For oral administration, the pharmaceutical compositions can be provided in the form of scored or unscored solid unit dosage forms.

A pharmaceutical composition comprising (1) lercanidipine hydrochloride, where the lercanidipine hydrochloride is selected from the group consisting of isolated lercanidipine hydrochloride crystalline Form (I), isolated lercanidipine hydrochloride crystalline Form (II), or combinations thereof of predetermined polymorph composition; and (2) at least one component selected from the group consisting of a pharmaceutically acceptable carrier or diluent, a flavorant, a sweetener, a preservative, a dye, a binder, a suspending agent, a dispersing agent, a colorant, a disintegrant, an excipient, a diluent, a lubricant, a plasticizer, and an edible oil. In a preferred embodiment, the pharmaceutical composition or dosage form comprises 0.1 to 400 mg lercanidipine hydrochloride. Preferably, the composition or dosage form comprises 1 to 200 mg lercanidipine hydrochloride, for all uses disclosed herein. More preferably, the composition or dosage form comprises 5 to 40 mg lercanidipine hydrochloride. Smaller amounts may be selected when a preferred enantiomer having higher activity for a particular therapeutic goal is used.

The pharmaceutical composition or unit dosage form may be administered in a single daily dose, or the total daily dosage may be administered in divided doses. In addition, co-administration or sequential administration of other active agents may be desirable. The polymorphs and mixtures thereof of the invention may be combined with any known drug therapy, preferably for treatment of hypertension. For example, bimodal therapy involving in addition a diuretic, a β-receptor blocker, an ACE inhibitor or an angiotensin II receptor antagonist is contemplated by the present invention (see, e.g., U.S. Provisional Application No. 60/344,601, filed Oct. 23, 2001 and Italian Application No. MI 2001 A 002136 filed Oct. 16, 2001).

For combination therapy the compounds may initially be provided as separate dosage forms until an optimum dosage combination and administration regimen is achieved. Therefore, the patient may be titrated to the appropriate dosages for his/her particular hypertensive condition. After the appropriate dosage of each of the compounds is determined to achieve a decrease of the blood pressure without untoward side effects, the patient then may be switched to a single dosage form containing the appropriate dosages of each of the active agents, or may continue with a dual dosage form.

The exact dosage and administration regimen utilizing the combination therapy of the present invention is selected in accordance with a variety of factors including type, species, age, weight, sex and medical condition of the patient; the severity and etiology of the hypertension to be treated; the route of administration; the renal and hepatic function of the patient; the treatment history of the patient; and the responsiveness of the patient. Optimal precision in achieving concentrations of compounds within the range that yields efficacy without toxicity requires a regimen based on the kinetics of the drug's availability to target sites. This involves a consideration of the absorption, distribution, metabolism, excretion of a drug, and responsiveness of the patient to the dosage regimen. However, such fine tuning of the therapeutic regimen is routine in light of the guidelines given herein.

A pharmaceutical composition for parenteral administration contains not below 0.1%, preferably from about 0.5% to about 30%, by weight of a polymorph or mixture of the present invention, based upon the total weight of the pharmaceutical composition. Individual isolated polymorphs are preferred for parenteral administration.

Generally, transdermal dosage forms contain from about 0.01% to about 100% by weight of the active agents, based upon 100% total weight of the dosage.

In a preferred embodiment of the present invention, the composition is administered daily to the patient. In a further preferred embodiment, the pharmaceutical composition or dosage form 0.1 to 400 mg lercanidipine hydrochloride. Preferably, the composition or dosage form comprises 1 to 200 mg lercanidipine hydrochloride. More preferably, the composition or dosage form comprises 5 to 40 mg lercanidipine hydrochloride.

EXAMPLES

The following examples of preparation of lercanidipine hydrochloride crude Forms (A) and (B) and crystalline Forms (I) and (II) are now disclosed for illustrative non-limiting purposes, together with the results of DSC analysis and solubility, stability and hygroscopicity tests; the bioavailability tests for the new crystalline forms are also disclosed.

Example 1

Initial Preparation

Thionyl chloride (36 g) diluted in ethyl acetate (25 g) was slowly added to a solution of 2,6-dimethyl-5-methoxycarbonyl-4-(3-nitrophenyl)-1,4-dihydropyridine-3-carboxylic acid (90 g) prepared, e.g., as disclosed in German patent DE 2847 237, in dimethylformamide (115 g) and ethyl acetate (396 g), keeping temperature between −1 and +1° C. A solution of 2, N-dimethyl-N-(3,3-diphenylpropyl)-1-amino-2-propanol (84 g) in ethyl acetate (72 g) was slowly added to the mixture thus obtained. The whole was kept under stirring at the same temperature for 3 hours. The mixture was then heated to 20–25° C. and kept under stirring for 12 hours. Water (340 ml) was then added, the whole was stirred for 30 min and after settling the aqueous phase was discarded. The organic phase was washed again with water (340 ml).

Example 2

Crude Lercanidipine Hydrochloride Form (A)

The organic phase obtained from Example 1 was then subjected to azeotropic distillation under vacuum at about 250 mmHg, without going above a temperature of 60° C. After removing about 50 ml of water, the solution was concentrated to about ⅓ of the initial volume in the same conditions of temperature and pressure and then brought to its initial volume with fresh ethyl acetate until the K.F. value (Karl Fisher value) was about 0.10–0.15%. The final suspension was cooled to 0–5° C. The solid was filtered, suspended in ethyl acetate (350 g) and stirred at 60–65° C. for 1 hour. The whole was cooled to 5–10° C. and then filtered. The solid was dried in an oven at 70° C. 133 g of dry raw lercanidipine hydrochloride Form (A) was obtained (75% yield), DSC peak 150–152° C.

Example 3

Crude Lercanidipine Hydrochloride Form (B)

The organic phase obtained at the end of Example 1 was heated under reflux (70–75° C.) and the water contained in the solution was removed with a Dean Stark apparatus (Spaziani Rolando, Nettuno, Rome, Italy) until a K.F. value of about 2% was obtained. The whole was then distilled at atmospheric pressure to reach ¾ of initial volume. The solution was brought to its initial volume by adding fresh ethyl acetate. The K.F. value at the end of this operation was 0.9–1.1%. The final solution was cooled to 0–5° C. A solid slowly precipitates which was filtered. The solid thus obtained was suspended in ethyl acetate (350 g) and stirred at 60–65° C. for 1 hour. The whole was cooled to 5–10° C., then filtered and dried in an oven at 70° C., thus obtaining 133 g of crude lercanidipine hydrochloride Form (B), DSC peak 131–135° C.; 75% yield.

Example 3A

Crude Lercanidipine Hydrochloride Form (B)

The organic phase obtained at the end of Example 1 was heated under reflux (70–75° C.) and the water contained in the solution was removed with a Dean Stark apparatus until a K.F. value of about 2% was obtained. The whole was then distilled at atmospheric pressure to reach ¾ of initial volume. The solution was brought to its initial volume by adding fresh ethyl acetate. The K.F. value at the end of this operation was 0.9–1.1%. The final solution was cooled to 20° C., seeded with 0.1% of crude lercanidipine hydrochloride Form (B) and cooled to 0–5° C. A solid slowly precipitated and was then filtered. The solid thus obtained was suspended in ethyl acetate (350 g) and stirred at 60–65° C. for 1 hour. The whole was cooled at 5–10° C., then filtered and dried in an oven at 70° C. for 24 hours, thus obtaining 133 g of crude lercanidipine hydrochloride Form (B), DSC peak 131–135° C.; 75% yield.

Example 4

Preparation of Lercanidipine Hydrochloride Crystalline Form (I)

In separate representative experiments, 100 g of crude lercanidipine hydrochloride Form (A), (B), or (C) was loaded into a reactor, followed by 400 ml of 2-propanol. The mixture was heated under strong reflux and under stirring, thus obtaining an almost complete dissolution of the crude substance. The mixture was hot filtered to eliminate a slight opalescence and the clear solution kept under stirring was cooled to 40° C. Temperature was then set at 35° C. The whole was kept for 24 hours under stirring at 35° C., then temperature was set at 30° C., and stirring was continued at said temperature for another 24 hours. The solid was filtered at 30° C. and washed with 50 ml of 2-propanol, then dried in an oven at 70° C. under vacuum for 24 hours. Weight of dry product in each case was (lercanidipine HCl (I)) 90 g (HPLC purity of the product in Form (I) >99.5%).

Example 4A

Preparation of Lercanidipine Hydrochloride Crystalline Form (I)

In separate representative experiments, 100 g of crude lercanidipine hydrochloride Form (A), (B), or (C) was loaded into a reactor, followed by 400 ml of 2-propanol. The mixture was heated under strong reflux and under stirring, thus obtaining an almost complete dissolution of the crude substance. The mixture was hot filtered to eliminate a slight opalescence and the clear solution kept under stirring is slowly cooled to 40° C. Precipitation was then triggered with 100 mg of lercanidipine hydrochloride Form (I) and temperature was set at 35° C., keeping the mixture under stirring. The whole was kept for 24 hours under stirring at 35° C., then temperature was set at 30° C., keeping under stirring at said temperature for another 24 hours. The solid was filtered at 30° C. and washed with 50 ml of 2-propanol, then dried in an oven at 70° C. under vacuum for 24 hours. Weight of dry product (lercanidipine HCl (I)) was 90 g (HPLC purity of the product in Form (I) >99.5%).

Example 5

Preparation of Lercanidipine Hydrochloride Crystalline Form (1)

In independent preparations, 25 kg of crude lercanidipine hydrochloride, Form (A) or (B), and then 100 mL of 95% ethanol were loaded and brought to strong reflux under stirring. The solution was cooled under stirring at 20° C. and then seeded with crystalline Form (I). The whole was then cooled to a temperature between 10 and 15° C., keeping the reaction mixture under stirring for 4 days. The solid thus obtained was filtered and washed with 95% ethanol, the precipitate was filtered and dried in an oven under vacuum at 70° C. for 24 hours. 20.2 kg of product was obtained, corresponding to a yield of 81%; HPLC purity in Form (I) >99.5%. Comparable results are obtained with Form (C) as starting material.

Example 6

Preparation of Lercanidipine Hydrochloride Crystalline Form (II)

100 g of crude lercanidipine hydrochloride Form (C) and then 200 ml of acetonitrile was loaded into a reactor. The mixture was heated under strong reflux and under stirring, thus obtaining a complete dissolution. The mixture was brought to 20–30° C. under slight stirring and kept at said temperature for 24 hours. The precipitate was filtered and dried in an oven at 70° C. for 24 hours. 95 g of dry product was obtained, corresponding to a 95% yield; HPLC purity >99.5% in lercanidipine hydrochloride Form (II). Comparable results are obtained when lercanidipine hydrochloride Form (A) or (B) is used as starting material.

Example 7

Preparation of Lercanidipine Hydrochloride Crystalline Form (II)

In separate representative experiments, 100 g of crude lercanidipine hydrochloride Form (A), (B), or (C) in 200 ml of 95% ethanol was loaded into a reactor, the mixture thus obtained was heated under stirring and under strong reflux and then cooled at 25° C. always under stirring. The solution was kept at said temperature for 24 hours under stirring. The precipitate thus obtained was then filtered and dried in an oven at 70° C. for 24 hours. 90 g of Form (II), HPLC purity >99.5% was obtained.

Example 7A

Preparation of Lercanidipine Hydrochloride Crystalline Form (II)

25 g of lercanidipine HCl crude substance or Form (C) was dissolved at 60° C. in 100 ml of a mixture ethanol-$H_2O$ (8:2). The whole was filtered by gravity to eliminate the possible insoluble portion and diluted with 100 ml of $H_2O$. The solution thus obtained was stirred at 25° C. as such, or it was added with 0.1 g of lercanidipine hydrochloride Form (II) or it was sonicated for 6 seconds at 20 kHz and 100 Watts, always at 25° C. Whatever the choice, after 48 hours under stirring the precipitate thus formed was collected and dried in an oven at 70° C. for 24 hours, obtaining a 80–85% yield of Form (II). Comparable results are obtained using crude Forms (A) or (B) or lercanidipine hydrochloride crystalline Form (I) as starting material.

As an alternative, the initial clear solution is diluted with 100 ml of ethanol and seeded with lercanidipine hydrochloride Form (II) (0.1 g). After 48 hours with stirring at 25° C., 80% yield with respect to stoichiometric lercanidipine hydrochloride Form (II) is obtained.

Example 8

Preparation of Lercanidipine Hydrochloride Crystalline Form (II) in Aqueous Methanol In representative independent examples, 40 g of lercanidipine hydrochloride crude Form (C) or crystalline Form (I) was dissolved in 100 ml of methanol at 30° C. The whole was filtered by gravity to eliminate the possible insoluble portion and 25 ml of water was added. The solution thus obtained was stirred at 25° C. as such, or was mixed with 0.1 g of lercanidipine hydrochloride Form (II), or was sonicated for 6 seconds at 20 kHz and 100 Watts, always at 25° C. Whichever the choice, after 48 hours under stirring the precipitate thus formed was collected and dried, with yields of 80–85% with respect to stoichiometric lercanidipine hydrochloride Form (II). Comparable results are obtained using crude Form (A) or (B).

Example 9

Preparation of Lercanidipine Hydrochloride Crystalline Form (II) in Aqueous 1-propanol 60 g of lercanidipine HCl crude Form (C) was dissolved at 60° C. in 100 ml of 1-propanol-$H_2O$ (8:2). After filtering by gravity the possible insoluble portion the solution was cooled in two hours to 25° C. and stirred for 120 hours at said temperature, with or without sonication for 6 seconds at 20 kHz and 100 Watts. The precipitate thus formed was collected, obtaining 90% yield with respect to stoichiometric lercanidipine hydrochloride Form (II) after a drying step. Comparable results are obtained using crude Forms (A) or (B) or lercanidipine hydrochloride crystalline Form (I) as starting material.

Example 10

Preparation of Lercanidipine Hydrochloride Crystalline Form (II) in Aqueous 2-propanol 30 g of lercanidipine hydrochloride crude Form (C) was dissolved at 60° C. in 100 ml of 2-propanol-$H_2O$ (8:2). After filtering by gravity the possible insoluble portion the solution was cooled in two hours to 25° C. and stirred for 72 hours at said temperature, with or without sonication for 6 seconds at 20 kHz and 100 Watts. The precipitate thus formed was collected, obtaining 85% yield with respect to stoichiometric lercanidipine hydrochloride Form (II) after a drying step. The same result is obtained by stirring for 168 hours at 10° C. Comparable results are obtained using crude Forms (A) or (B) or lercanidipine hydrochloride crystalline Form (I) as starting material.

Example 11

Preparation of Lercanidipine Hydrochloride Crystalline Form (II) in Aqueous N-methylpyrrolidone A suspension of 50 g of lercanidipine hydrochloride crude Form (C) in 30 ml of N-methylpyrrolidone/water (1:1) was stirred at 20–25° C. for 12 days. The solid thus formed was collected by filtration and dried, yielding 40 g of lercanidipine hydrochloride Form (II). Comparable results are obtained using crude Forms (A) or (B) or lercanidipine hydrochloride crystalline Form (I) as starting material.

Example 12

DSC Analysis of Lercanidipine Hydrochloride Crystalline Forms (I) and (II)

DSC analysis measures changes that occur in a given sample with heating, wherein the changes identify transition phases. Enthalpy variations taking place in a transition phase are calculated on the basis of the area under the curve. The most common transition phases are melting and sublimation. The temperature at which transition starts, onset T, is given by the point in which the curve starts to deviate from the base line (flex point).

DSC of Form (I): 3.8 mg of Form (I) was placed in a golden pan of the apparatus Perkin Elmer DSC7. The heating speed during the test was 10° C./min.

DSC Form (II): 4.6 mg of Form (II) was placed in a golden pan of the apparatus Perkin Elmer DSC7. The heating speed during the test was 10° C./min.

Figure 2:
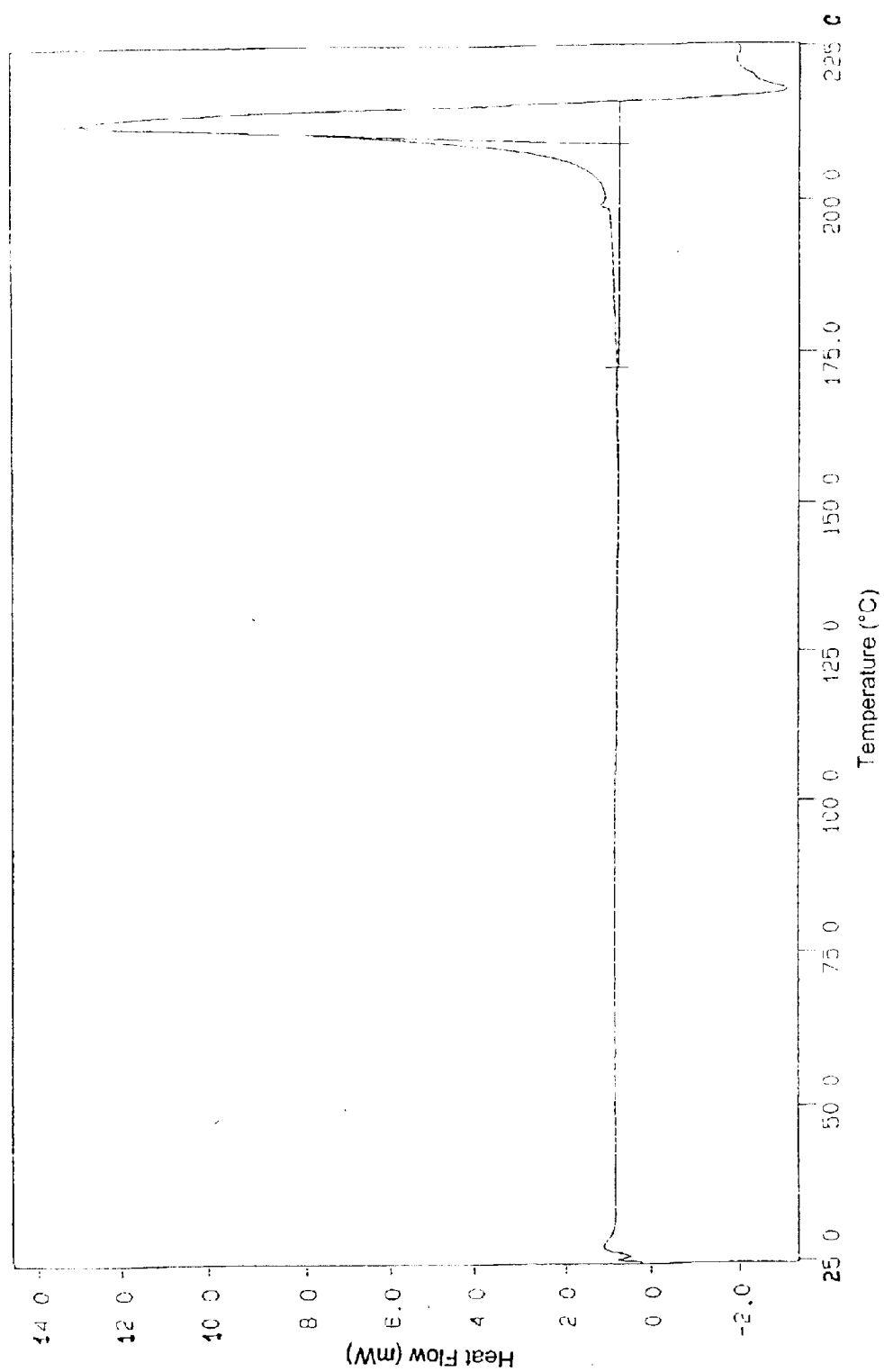
FIG. 2 is a graph of DSC analysis carried out on crystalline Form (II), according to the working conditions described in Example 12. The ordinate indicates heat flow in mW and the abscissa temperature in ° C.

The data are shown in FIGS. 1 and 2 and the characteristic points of the figures are briefly summarized in the following Table 1.

TABLE 1

| Compound | Melting T (Tpeak) [° C.] | Onset T [° C.] |
|---|---|---|
| Form (I) | 198.7 | 179.8 |
| Form (II) | 209.3 | 169.0 |

Immediately after melting of Form (I) or (II) an exothermic event due to salt decomposition can be observed.

Example 13

Thermogravimetry

A gravimetric analysis associated with an IR analysis was carried out on both crystalline Forms (I) and (II), and also on crude lercanidipine hydrochloride Form (A) and on crude lercanidipine hydrochloride Form (B), using a Netsch Thermomicrobalance 209 in combination with a spectrometer FTIR Bruker Vector 22.

Figure 3:
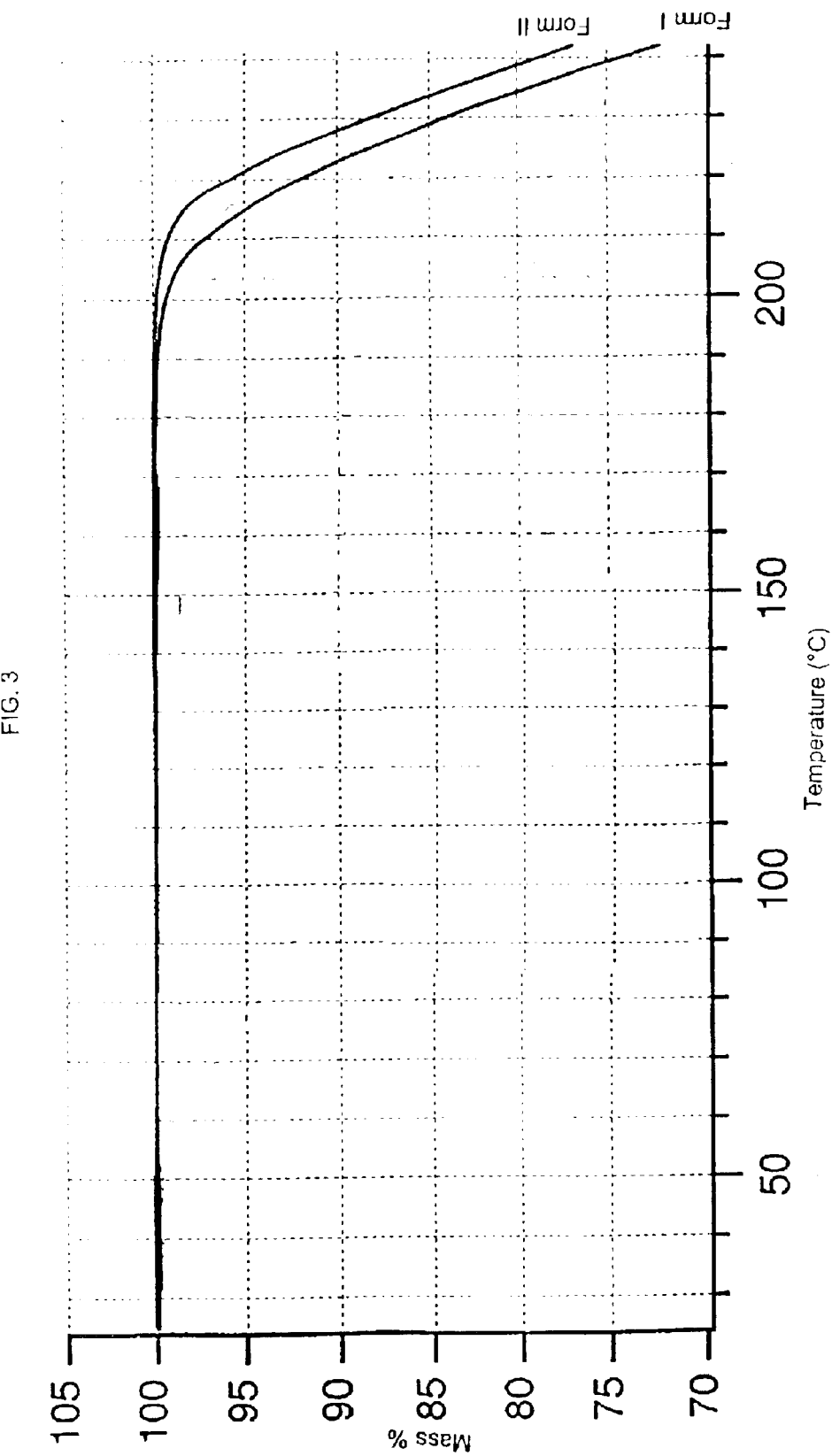
FIG. 3 is a graph of the results of the thermogravimetric tests carried out on Form (I) and Form (II), respectively, as described in Example 13. The abscissa indicates temperature in 0° C. and the ordinate indicates percent mass variation.

The tests were carried out according to the following working conditions: 2–5 mg of sample was heated in a steel crucible in nitrogen atmosphere, with a heating speed of 10° C./min. The results obtained with crystalline Forms (I) and (II) are shown in FIG. 3, from which it can be inferred that in both crystalline forms no weight loss can be observed up to their melting point (i.e., until about 190–200° C.).

During degradation, which takes places as indicated above after melting, a $CO_2$ loss can be observed.

Figure 19:
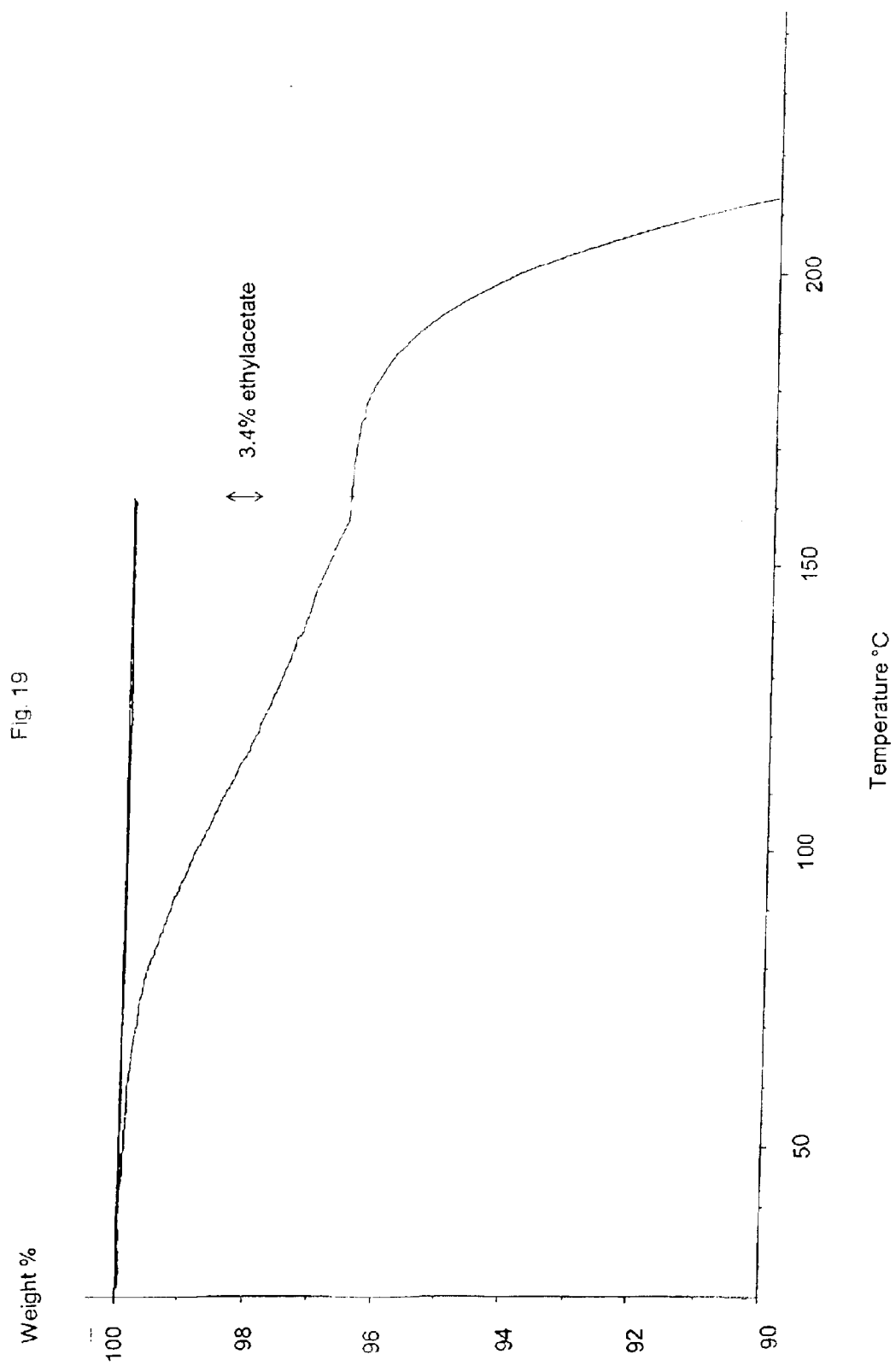
FIGS. 19 and 20 show the results of the thermogravimetric analysis carried out on crude lercanidipine hydrochloride Form (A) and on crude lercanidipine hydrochloride Form (B), respectively. In these figures, the abscissa indicates temperature (in ° C.) and the ordinate indicates percent mass variation.

The results obtained with crude lercanidipine hydrochloride Form (A) are shown in FIG. 19, where a weight loss of 3.4% can be observed in the temperature range 25–153° C. The volatile compound has been identified by its corresponding IR spectrum and is ethyl acetate. During degradation (T>170° C.) a small amount of ethyl acetate in gas phase could be observed.

Figure 20:
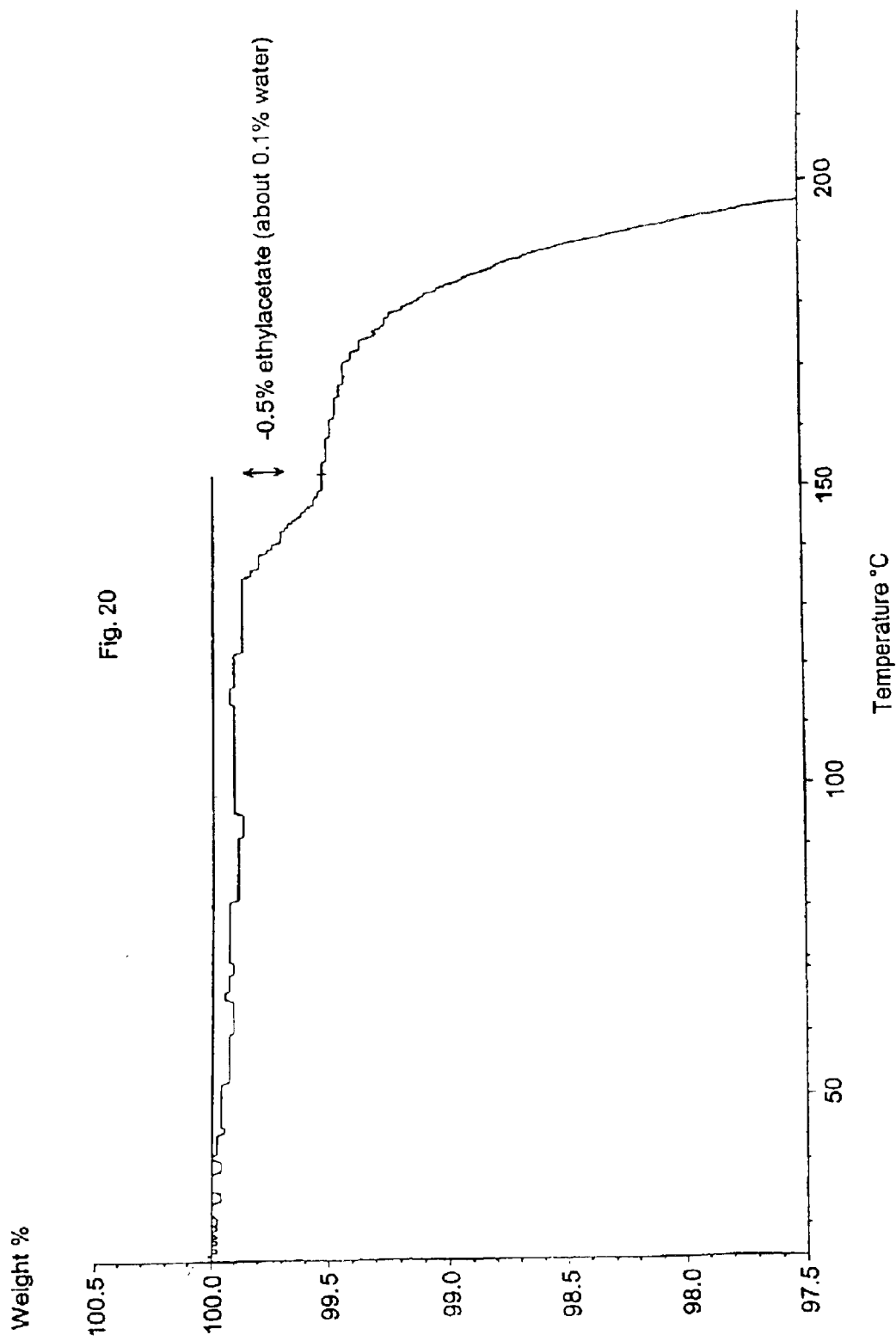

The results obtained with crude lercanidipine hydrochloride Form (B) are shown in FIG. 20, where a weight loss of 0.5% in temperature range 25–153° C. can be observed. The volatile compound identified with its corresponding IR spectrum is ethyl acetate (0.4%) and water (0.1%). During degradation (T>170° C.) a small amount of ethyl acetate in gas phase can be observed.

EXAMPLE 14

Hygroscopicity of Crystalline Forms (I) and (II)

The hygroscopicity of both crystalline Forms (I) and (II) was measured with DVS analysis by means of a water absorption analyzer (SURFACE MEASUREMENT SYSTEM, Marion, Buckinghamshire, UK) according to the following working conditions:

10–15 mg of Form (I) and (II) respectively were placed in a quartz sample-holder, placed in its turn on a microbalance, and the sample underwent humidity cycles between 0 and 95%, starting from 50% of relative humidity (25° C., relative humidity (RH): 50-95-0-95-0-50% at RH/h:5%).

Figure 13:
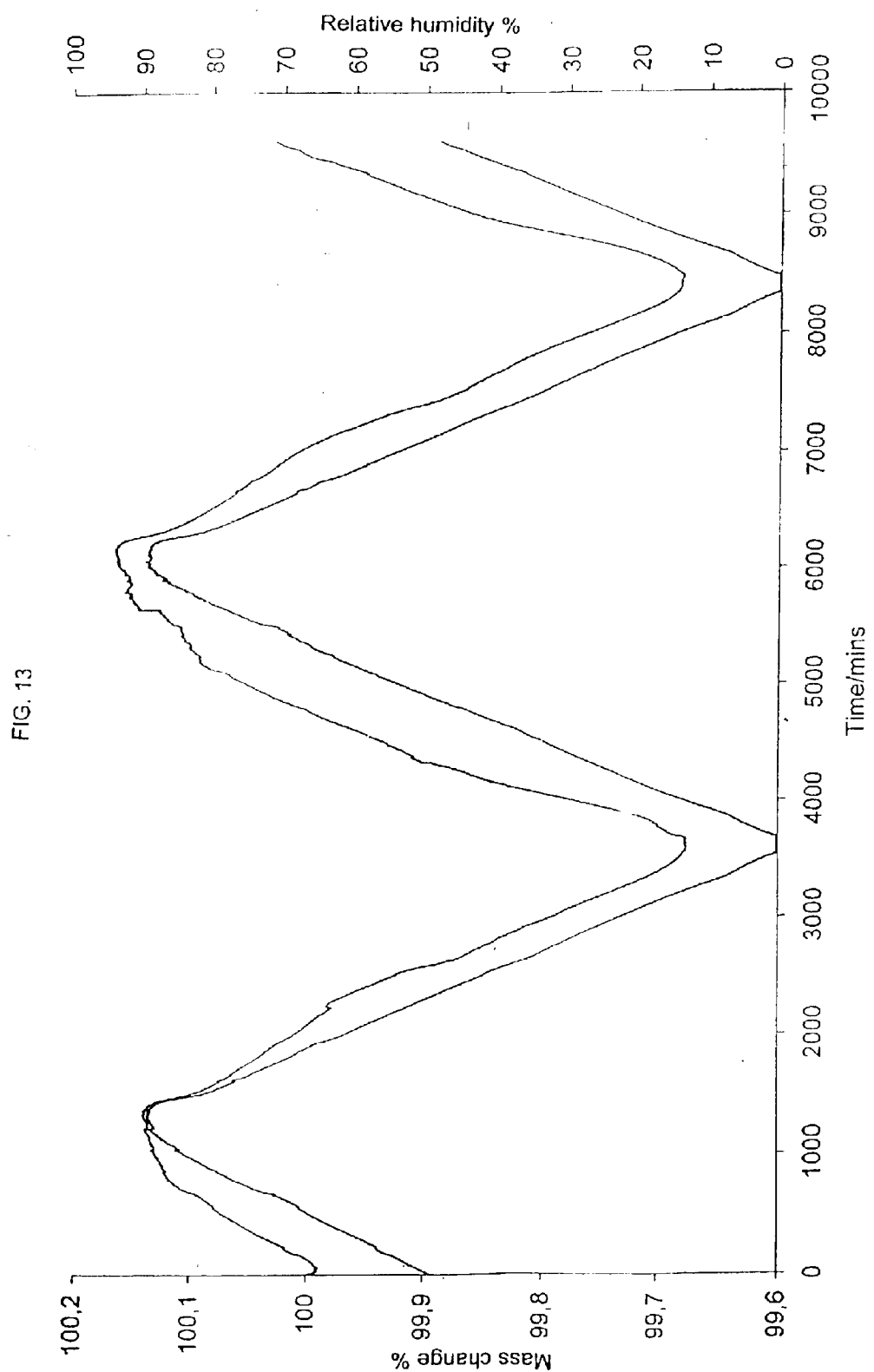
FIGS. 13 and 14 are plots of percent mass change as a function of time in hygroscopicity tests carried out on Forms (I) and (II) of lercanidipine hydrochloride, respectively. The ordinate on the left indicates percent mass changes and the ordinate on the right percent relative humidity; the abscissa indicates time in minutes. The protocol for the hygroscopicity tests are described in Example 14.
Figure 14:
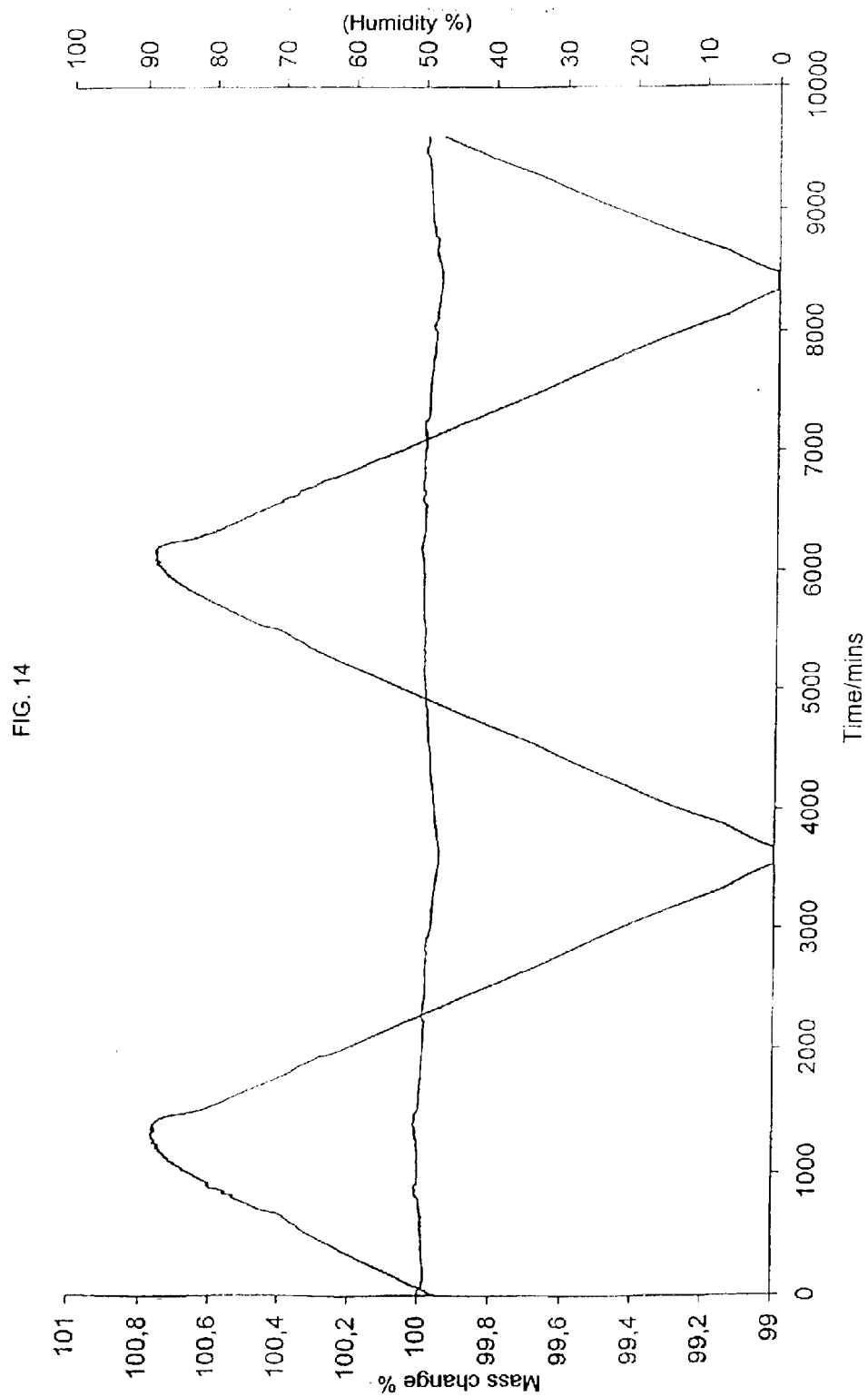
Figure 15:
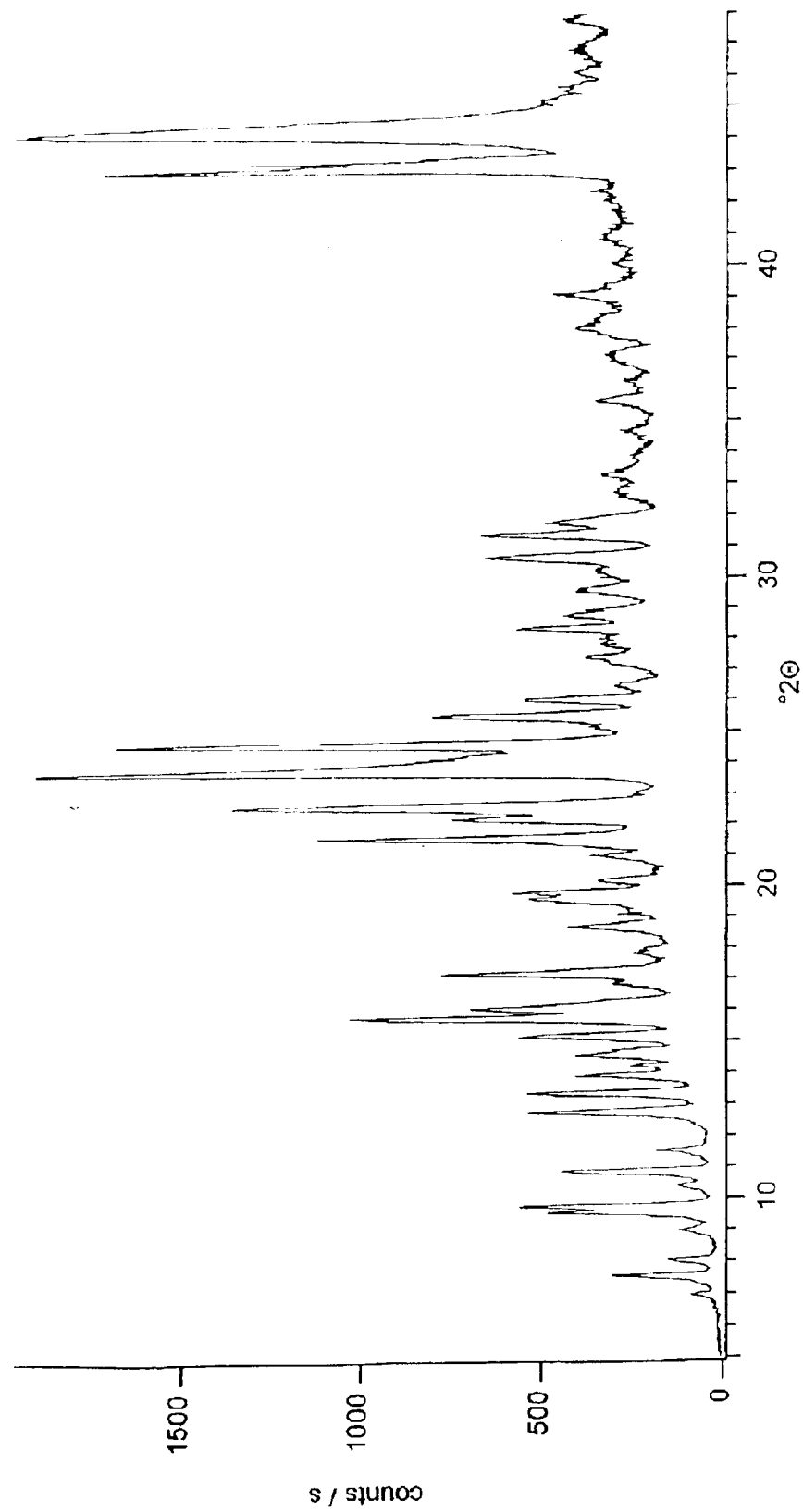
FIGS. 15 and 16 show X-ray diffraction spectra at wavelength Kα of crude lercanidipine hydrochloride Form (A) and of crude lercanidipine hydrochloride Form (B), respectively.
Figure 16:
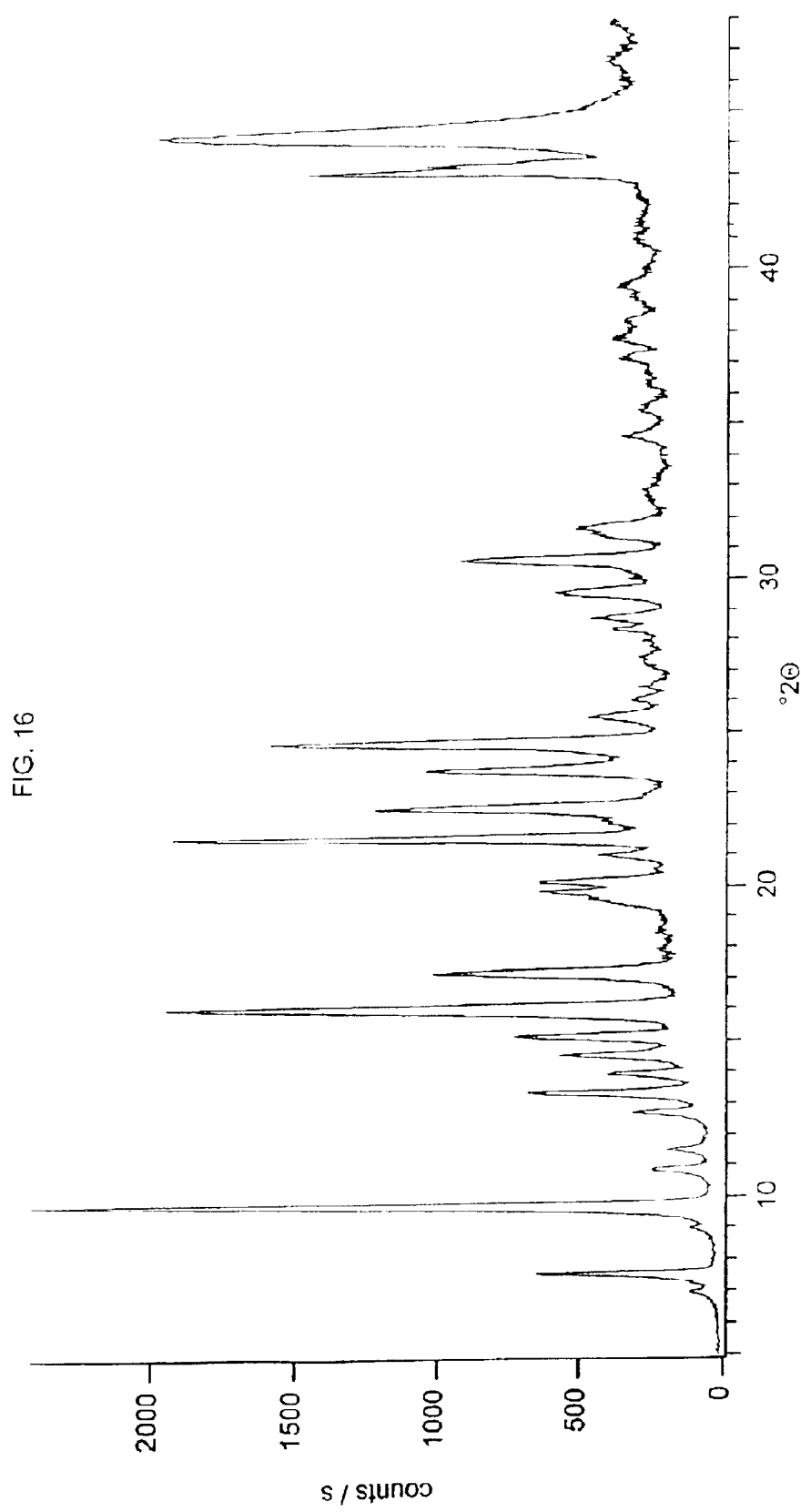
Figure 17:
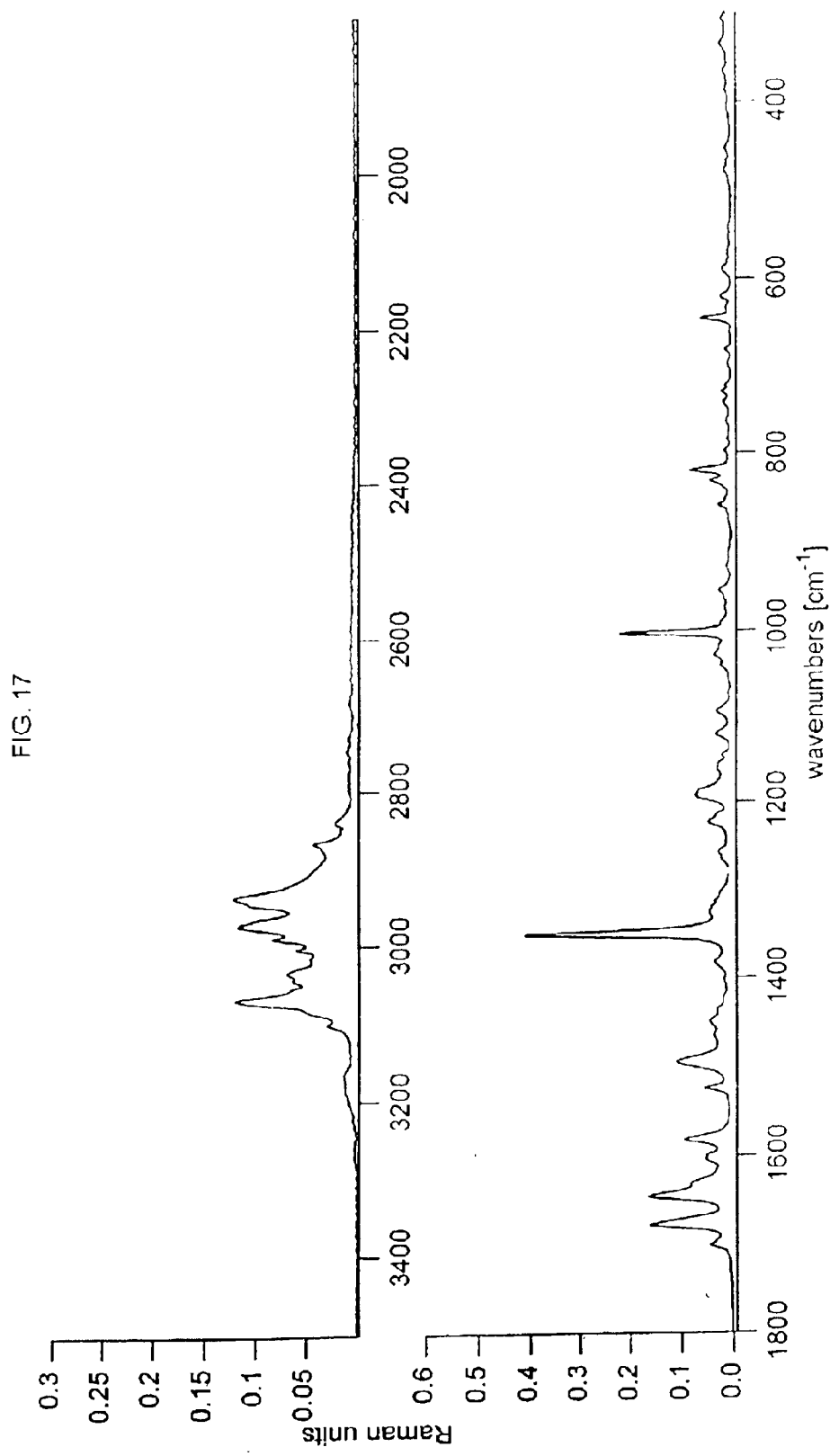
FIGS. 17 and 18 show Raman spectra of crude lercanidipine hydrochloride Form (A) and of crude lercanidipine hydrochloride Form (B), respectively, where the ordinate represents Raman units and the abscissa represents wave number ($cm^{-1}$).
Figure 18:
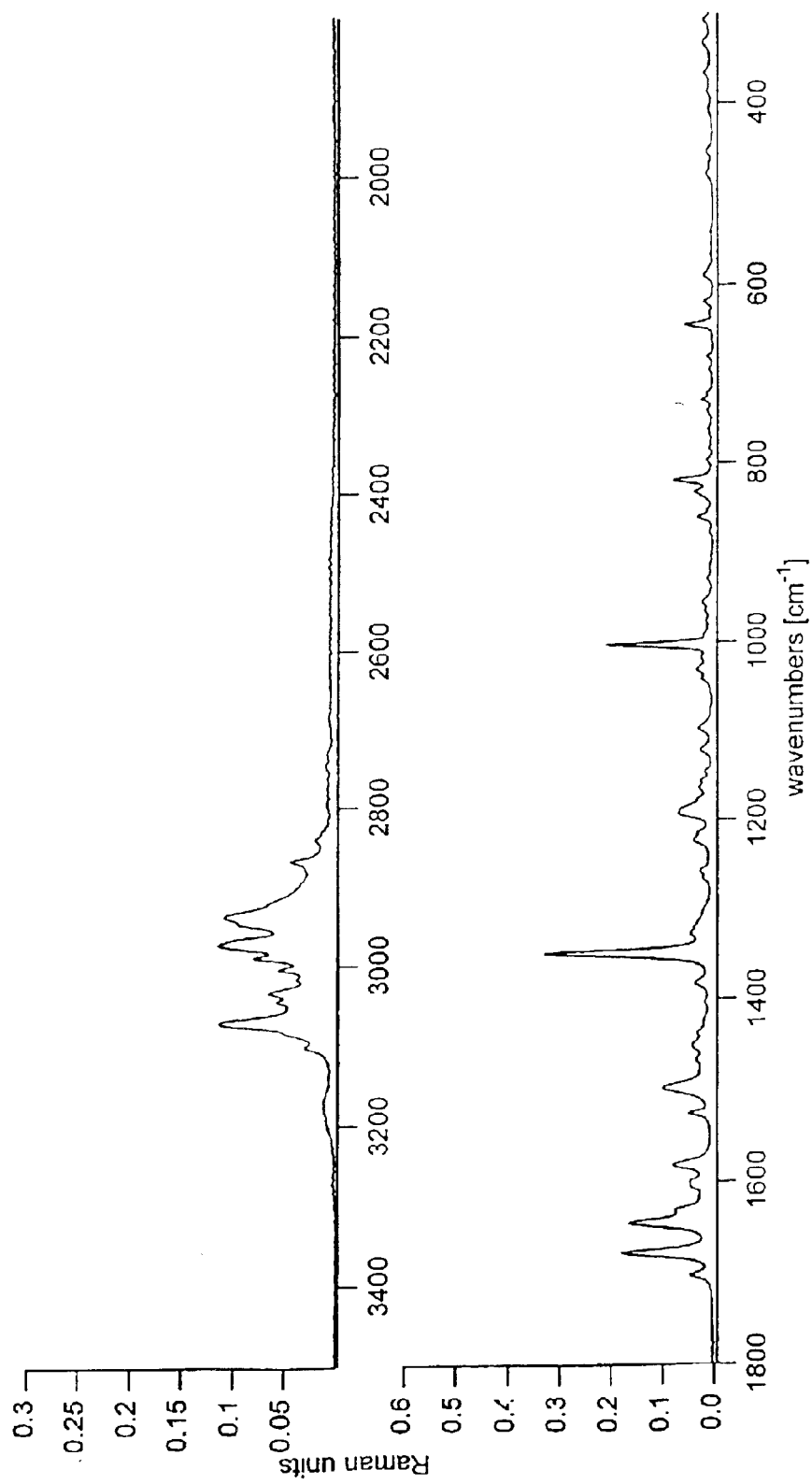

The results of the tests are shown in the diagrams of FIGS. 13 and 14.

14-1 Results Obtained with Crystalline Form (I)

The exposure of Form (I) to humidity in the DVS analyzer results in a mass change of +0.15% at 95% RH, and of −0.3% at 0% RH, with almost no hysteresis during mass increase and loss. These slight variations are probably due to a reversible surface absorption of water.

14-2 Results Obtained with Crystalline Form (II)

The exposure of Form (II) to humidity in DVS causes a negligible mass variation (<0.05%) in the whole RH range tested.

Example 15

Solubility of Crystalline Forms (I) and (II)

15.1 Solubility in Water and in Ethanol at Room Temperature

The solubility at 23° C. of both crystalline Forms (I) and (II) was evaluated by UV-Visible spectroscopy in bi-distilled water (at the pH value spontaneously reached by the system) and in absolute ethanol. The molar absorptivity had been previously determined in acetonitrile. The same molar absorptivity was considered for the determination in water and in ethanol. Solubility in water certainly depends on pH. The residual solid obtained by filtration of the suspension was immediately analyzed with Raman spectroscopy. The results are shown in the following Tables 2 and 3.

TABLE 2

| Solubility in water (about 40 mg/ml as initial condition). | | | |
|---|---|---|---|
| Starting material | Time [min] | Solubility [mg/ml] | Residual material |
| Form (I) | 5/25/45/990 | 0.4/0.5/0.5/0.5 | Form (I) |
| Form (II) | 5/25/45/990 | 0.2/0.2/0.3/0.3 | Form (II) |

TABLE 3

| Solubility in ethanol (100 mg/ml as initial condition) | | | |
|---|---|---|---|
| Starting material | Time [min] | Solubility [mg/ml] | Residual material |
| Form (I) | 15/45/120 | 28/27/27 | Form (I) |
| Form (II) | 15/45/120 | 11/12/12 | Form (II) |

Figure 4:
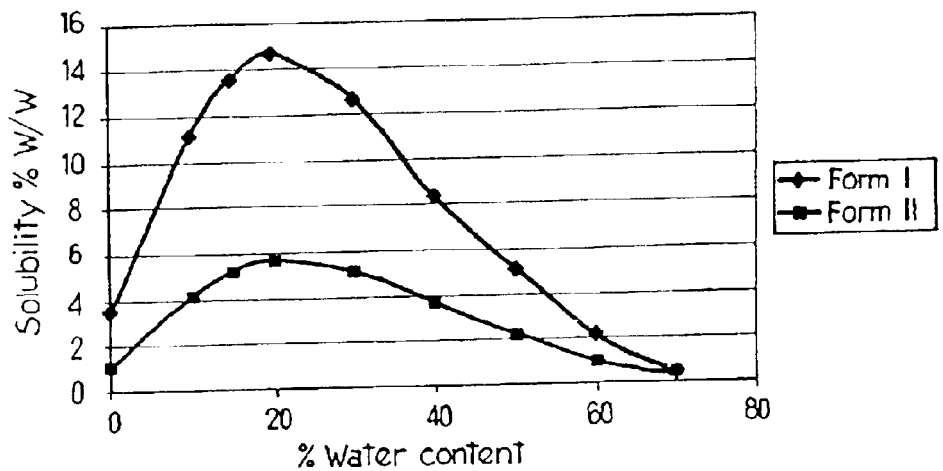
FIG. 4 is a graph of solubility at 25° C. of Forms (I) and (II) in ethanol at increasing water concentrations. The experiments are described in Example 15. The ordinate indicates % solubility expressed as w/w and the abscissa % by weight of water in ethanol.
Figure 5:
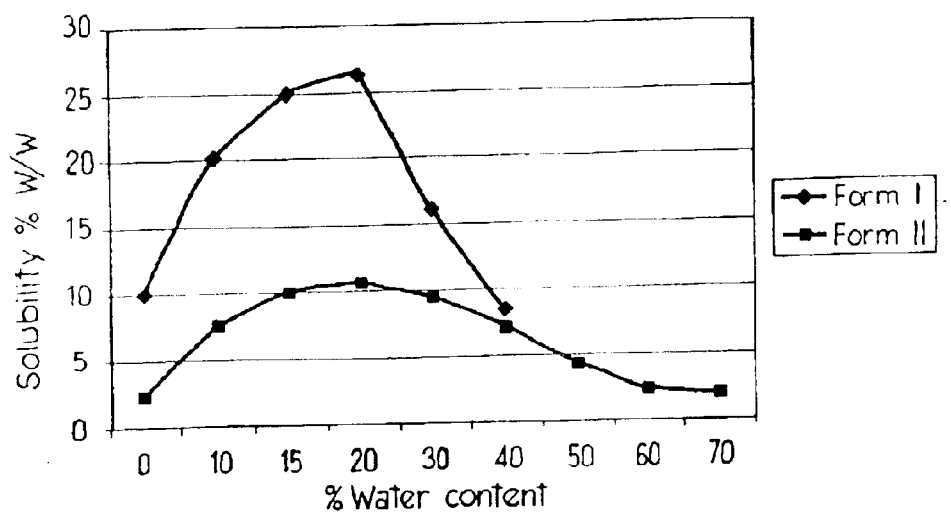
FIG. 5 is a graph of solubility at 40° C. of Forms (I) and (II) in ethanol at increasing water concentrations. The tests are described in Example 15. The ordinate indicates % solubility expressed as w/w and the abscissa % by weight of water in ethanol.
Figure 6:
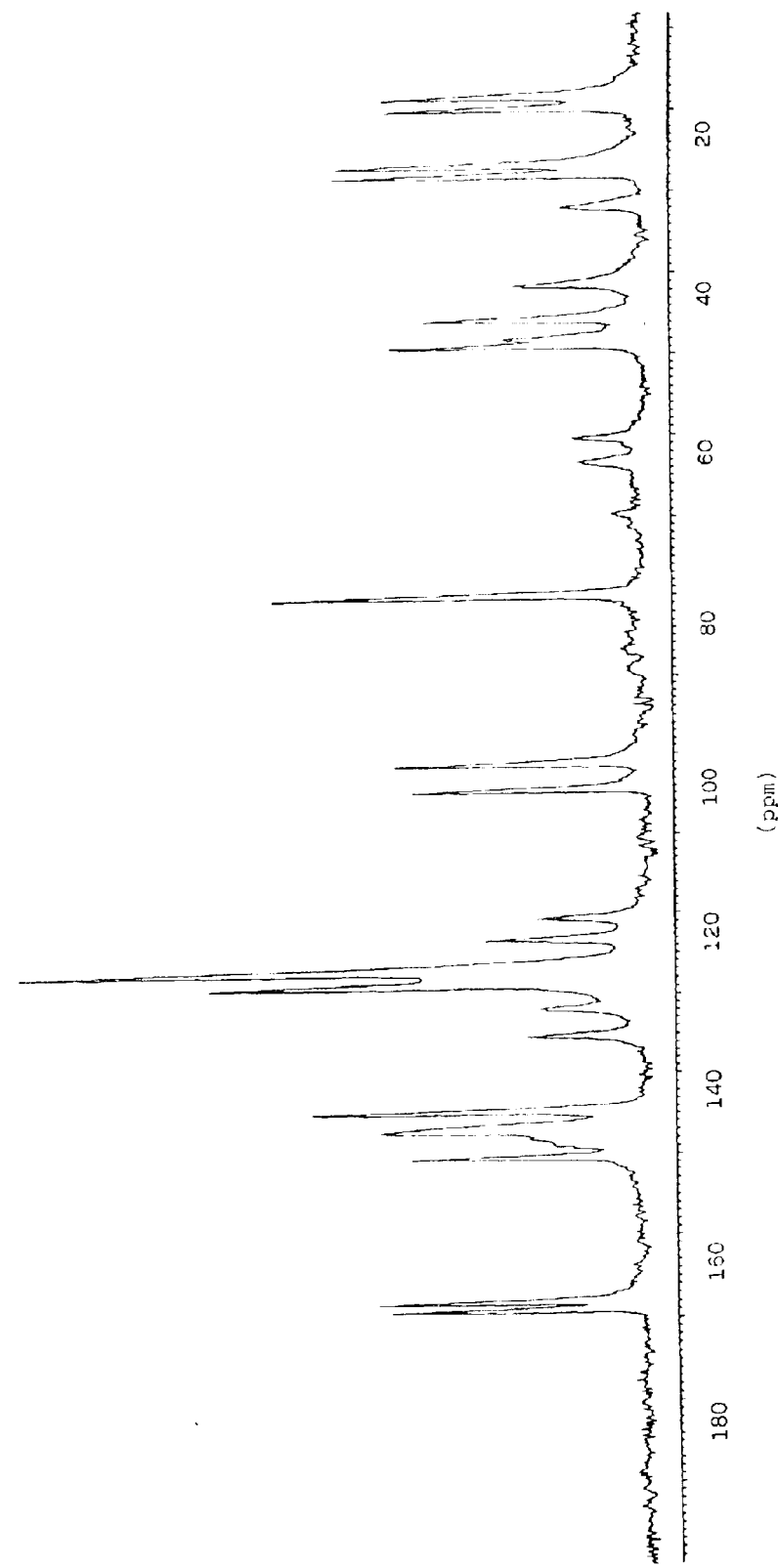
FIG. 6 shows $^{13}C$ NMR spectra in solid phase of crystalline Form (I). The signals and attributes of the corresponding carbon atoms can be found in Table 4.
Figure 7:
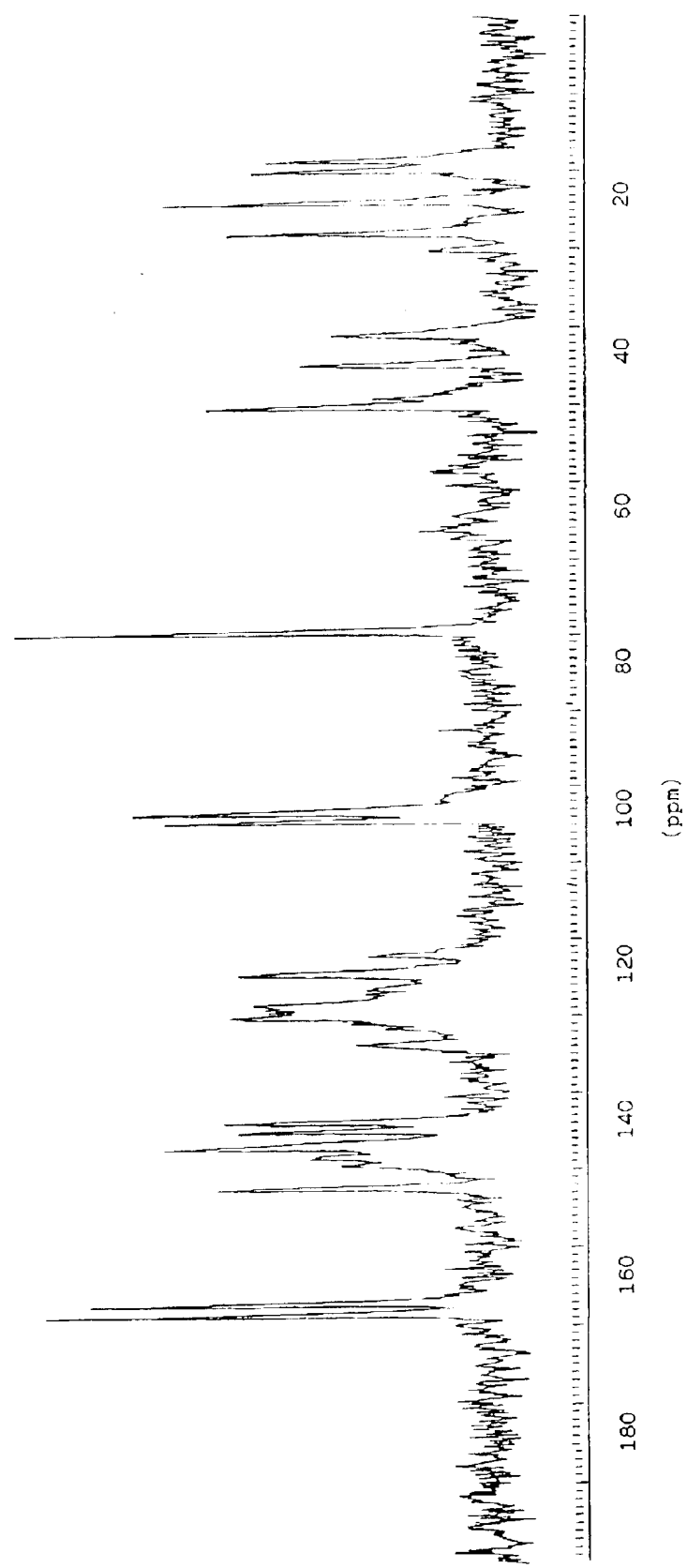
FIG. 7 shows $^{13}C$ NMR spectra in solid phase of crystalline Form (II). The signals and attributes of the corresponding carbon atoms can be found in Table 5.
Figure 8:
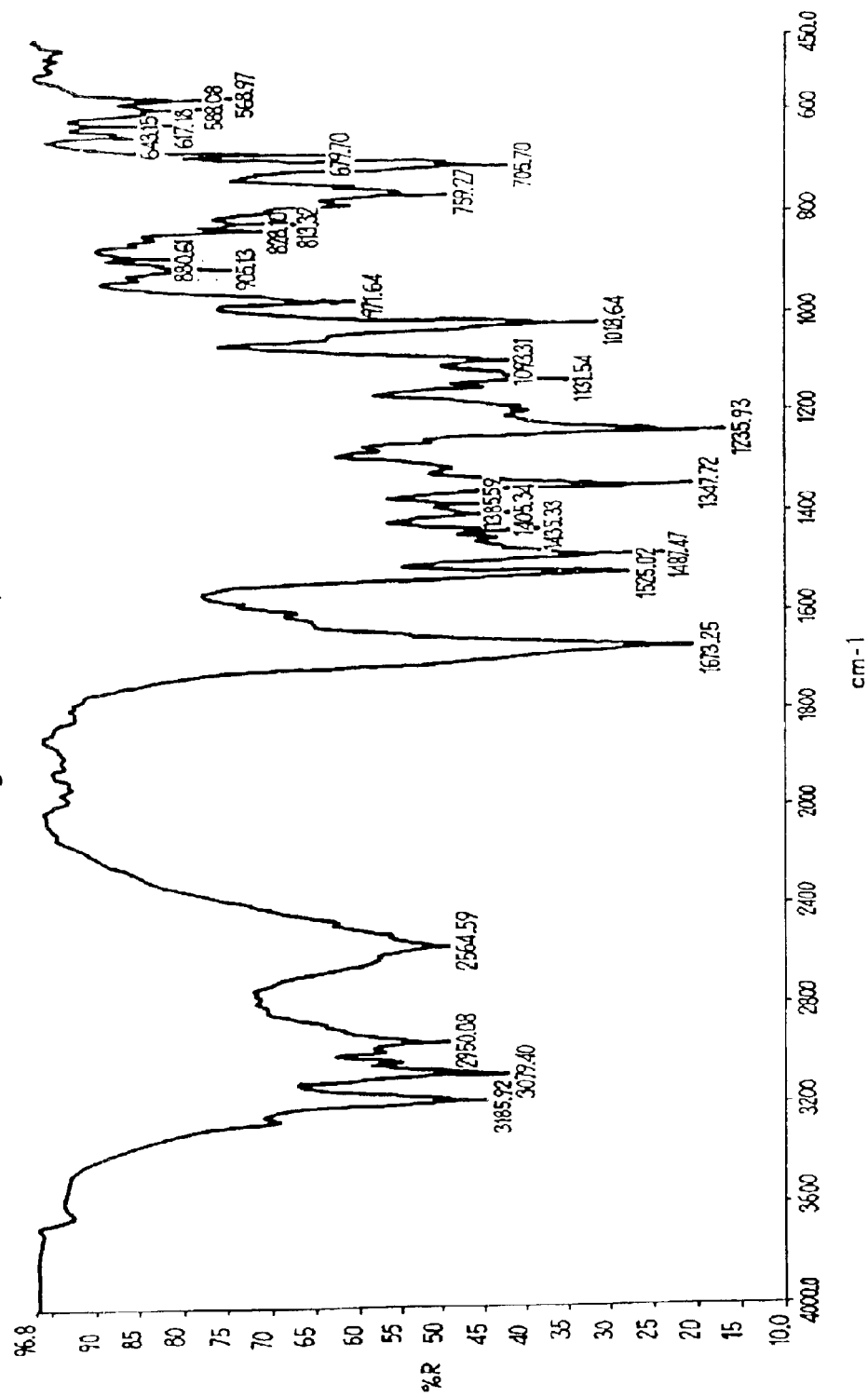
FIG. 8 shows IR spectra of Form (I). The signal and corresponding attributes can be found in Table 6.
Figure 9:
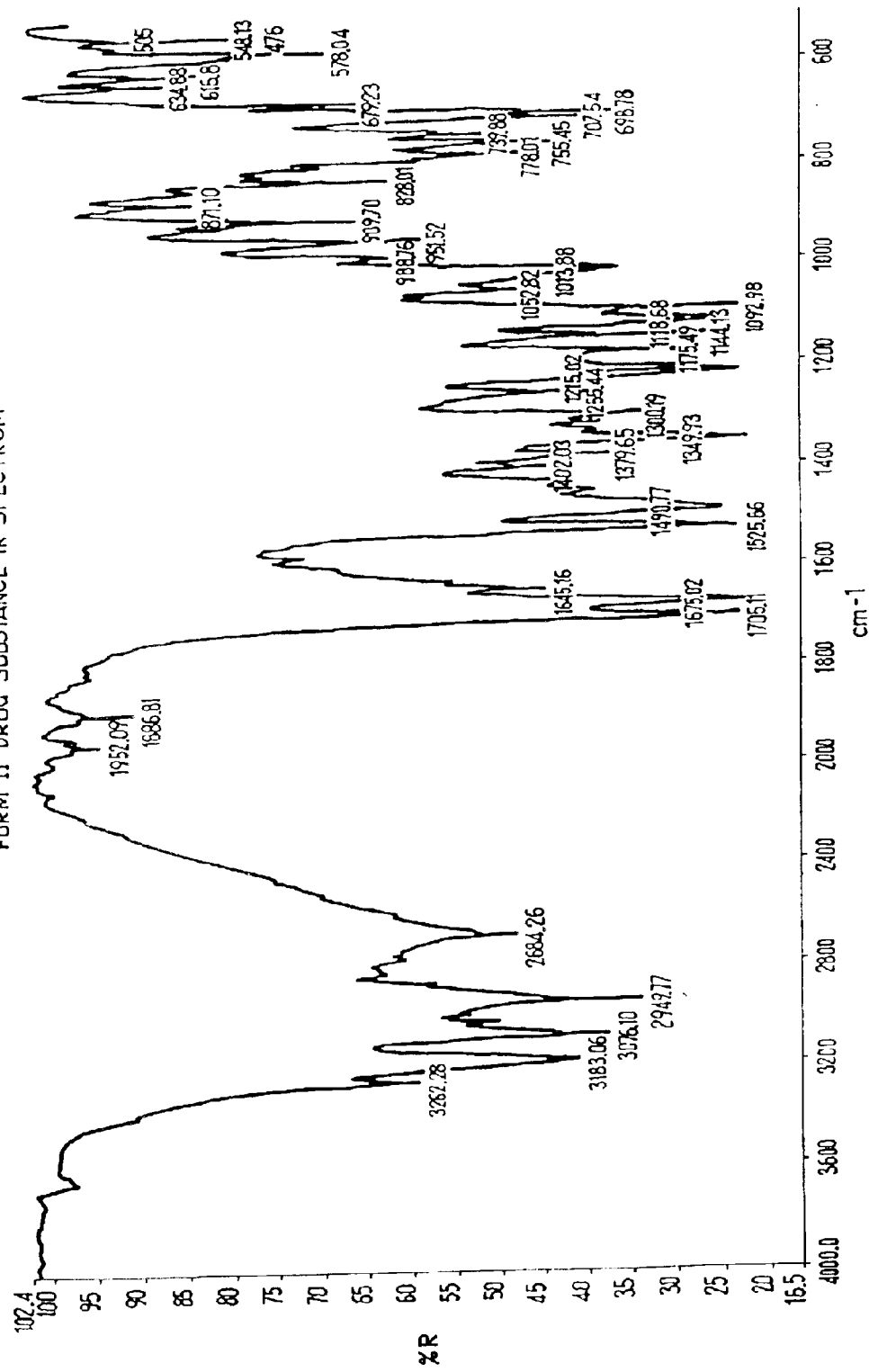
FIG. 9 shows IR spectra of Form (II). The signal and corresponding attributes can be found in Table 7.

Form (II) is less soluble than Form (I) in both solvents.
15.2 Solubility in Mixtures of Water-ethanol at 25° C. and at 40° C., with Increasing Water Concentrations FIGS. 4 and 5 show solubility in water-ethanol at 25° C. and at 40° C. of Form (I) and of Form (II). The maximum solubility is reached for both forms, at both temperatures, when water concentration is of 20%. Also in this case the solubility of crystalline Form (I) is higher than that of crystalline Form (II).

Example 16

Solid Phase $^{13}$C-NMR Studies

The high resolution $^{13}$C-NMR solid phase spectra were carried out with the Bruker, ASX300 Instrument equipped with a 7 mm Rotor accessory, using several combined techniques:

Magic Angle Spinning (MAS)

About 300 mg of the sample was placed in the rotor spinning at 4.3 kHz around an axis oriented at the magic angle (54° 70') to the magnetic field to overcome the dipolar bradening caused by CSA (Chemical Shift Anisotropy). The experiments were conducted at room temerature.

Dipolar Coupling

Since much of line broadening in $^{13}$C spectra of organic solids is due to coupling to protons, it was removed by heteronuclear decoupling (decoupling power level was almost 1 Kilowatt).

Cross Polarization (CP)

Cross polarization allowed carbon magnetization from larger proton magnetization via the dipolar coupling to increase signal intensity.

Total Suppression of Sidebands (TOSS)

TOSS was performed using spin-echoes synchronized with the rotation of the sample to cause phase alteration of the spinning sidebands, resulting in cancellation when successive spectra were added together.

Crystalline Forms (I) and (II) show different $^{13}$C-NMR spectra in solid phase. The signals (chemical shift) and attribution of the corresponding carbon atoms (as numbered in the formula of lercanidipine hydrochloride shown below) are represented in the following Tables 4 and 5, respectively.

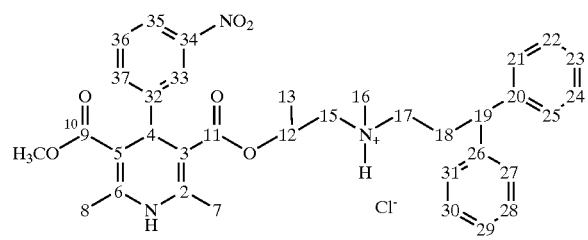

TABLE 4

Lercanidipine hydrochloride crystalline Form (I)

| Chemical shift (δ, ppm) | Attribution of carbon atoms |
|---|---|
| 168.7; 167.7 | 9; 11 or 11; 9 |
| 150.1 to 120.4 | 2; 6 and 20 to 37 |
| 104.3; 100.9 | 3; 5 or 5; 3 |
| 79.7 | 12 |
| 63.0; 60.1 (weak) | 15; 17 or 17; 15 |
| 48.6 | 10 |
| 47.7 | 16 |
| 45.4 | 19 |
| 41.1 | 4 |
| 31.6 | 18 |
| 27.7; 26.4 | 13; 14 or 14; 13 |
| 19.6; 18.0 | 7; 8 or 8; 7 |

TABLE 5

Lercanidipine hydrochloride crystalline Form (II)

| Chemical shift (δ, ppm) | Attribution of carbon atoms |
|---|---|
| 168.1; 166.6 | 9; 11 or 11; 9 |
| 151.9; 121.9 | 2; 6 and from 20 to 37 |
| 104.0; 102.8 | 3; 5 or 5; 3 |
| 79.0 | 12 |
| 66.0; 58.0 (weak) | 15; 17 or 17; 15 |
| 49.7 | 10 |
| 48.8 | 16 |
| 44.3 | 19 |
| 40.5 | 4 |
| 29.8 | 18 |
| 27.6; 23.5 | 13; 14 or 14; 13 |
| 19.6; 18.3 | 7; 8 or 8; 7 |

Example 17

IR Studies

The IR (infrared) spectra were recorded in KBr powder by Diffuse Reflectance Technique using a Perkin Elmer Spectrum-one instrument. IR spectra, whose wave lengths and corresponding attribution are shown in the following Tables 6 and 7, are clearly different for the new Forms (I) and (II).

TABLE 6

IR spectrum in KBr powder of lercanidipine hydrochloride Form (I)

| Wavelength (cm$^{-1}$) | Attribution |
|---|---|
| 3186 | NH stretching |
| 3100–2800 | Alkyl and phenyl stretching |
| 2565 | N$^+$H stretching |
| 1673 | C=O stretching |
| 1525; 1348 | Asymmetric and symmetric stretching of NO$_2$ group |
| 1405; 1386 | Bending of geminal methyl groups |
| 785–685 | Out-of-plane bending of 5 and 3 adjacent hydrogens on aromatic rings |

TABLE 7

IR spectrum in KBr powder of lercanidipine hydrochloride Form (II)

| Wavelength (cm$^{-1}$) | Attribution |
|---|---|
| 3183 | NH stretching |
| 3100–2800 | Alkyl and phenyl stretching |
| 2684 | N$^+$H stretching |
| 1705; 1675 | C=O stretching |
| 1526; 1350 | Asymmetric and symmetric stretching of NO$_2$ group |
| 1402; 1380 | Bending of geminal methyl groups |
| 800–680 | Out-of-plane bending of 5 and 3 adjacent hydrogens on aromatic rings |

Example 18

Raman Spectra

A Bruker FT-Raman RFS100 Spectrophotometer was utilized under the following typical conditions: about 10 mg sample (without any previous treatment), 64 scans 2 cm$^{-1}$ resolution, 100 mW laser power, Ge-detector.

The following Tables 8 and 9 show the most significant peaks of Raman spectra of Form (I) and Form (II), respectively.

TABLE 8

Raman spectrum of crystalline Form (I)

| Wave number (cm$^{-1}$) | Peak intensity* |
| --- | --- |
| 3054 | M |
| 3040 | M |
| 2981 | M |
| 2941 | M |
| 1675 | S |
| 1646 | M |
| 1583 | M |
| 1489 | M |
| 1349 | Vs |
| 1236 | M |
| 1005 | S |
| 821 | M |
| 174 | M |
| 98 | S |
| 73 | Vs |

*M = moderate; S = strong, Vs = very strong

TABLE 9

Raman spectrum of crystalline Form (II)

| Wave number (cm$^{-1}$) | Peak intensity* |
| --- | --- |
| 3074 | M |
| 3064 | M |
| 3055 | M |
| 3048 | M |
| 3030 | M |
| 2973 | M |
| 2940 | M |
| 1675 | S |
| 1647 | S |
| 1630 | M |
| 1584 | M |
| 1489 | M |
| 1351 | Vs |
| 1005 | M |
| 995 | M |
| 103 | Vs |
| 85 | S |

*M = moderate; S = strong, Vs = very strong

Example 19

Bioavailability of Crystalline Forms (I) and (II)

19a—Dog

A study was carried out on six Beagle dogs to evaluate the bioavailability of crystalline Forms (I) and (II).

The products, in micronized form, were administered orally by hard gelatin capsules filled up with the active agent, Form (I) and (II), at a dosage of 3 mg/kg, administered once in the morning of the day of the experiment.

Blood samples were taken at given times and plasma concentrations of lercanidipine were determined with a stereoselective analytical method HPLC-MS/MS, according to the following working conditions;

Lercanidipine was extracted from dog plasma by means of a liquid-liquid extraction with a mixture of n-hexane and ethyl ether. The dry residue of the organic phase was taken up with a mixture of methanol and water and a liquid-phase chromatographic separation (LC) was carried out; the two enantiomers of lercanidipine were separated on a CHIRO-BIOTIC V column (Vancomycin) (particle size 5 m, column size 150×4.6 mm (ASTEC, NJ, USA)) and were detected with a mass spectrometer (MS/MS) by using an electrospray technique.

The analytical method was validated in a concentration range between 0.1 and 20 ng/ml of plasma for both enantiomers. The method has shown to be specific with an accuracy of 15%. The average concentrations of lercanidipine in the tables represent the sum of both enantiomers.

Figure 10:
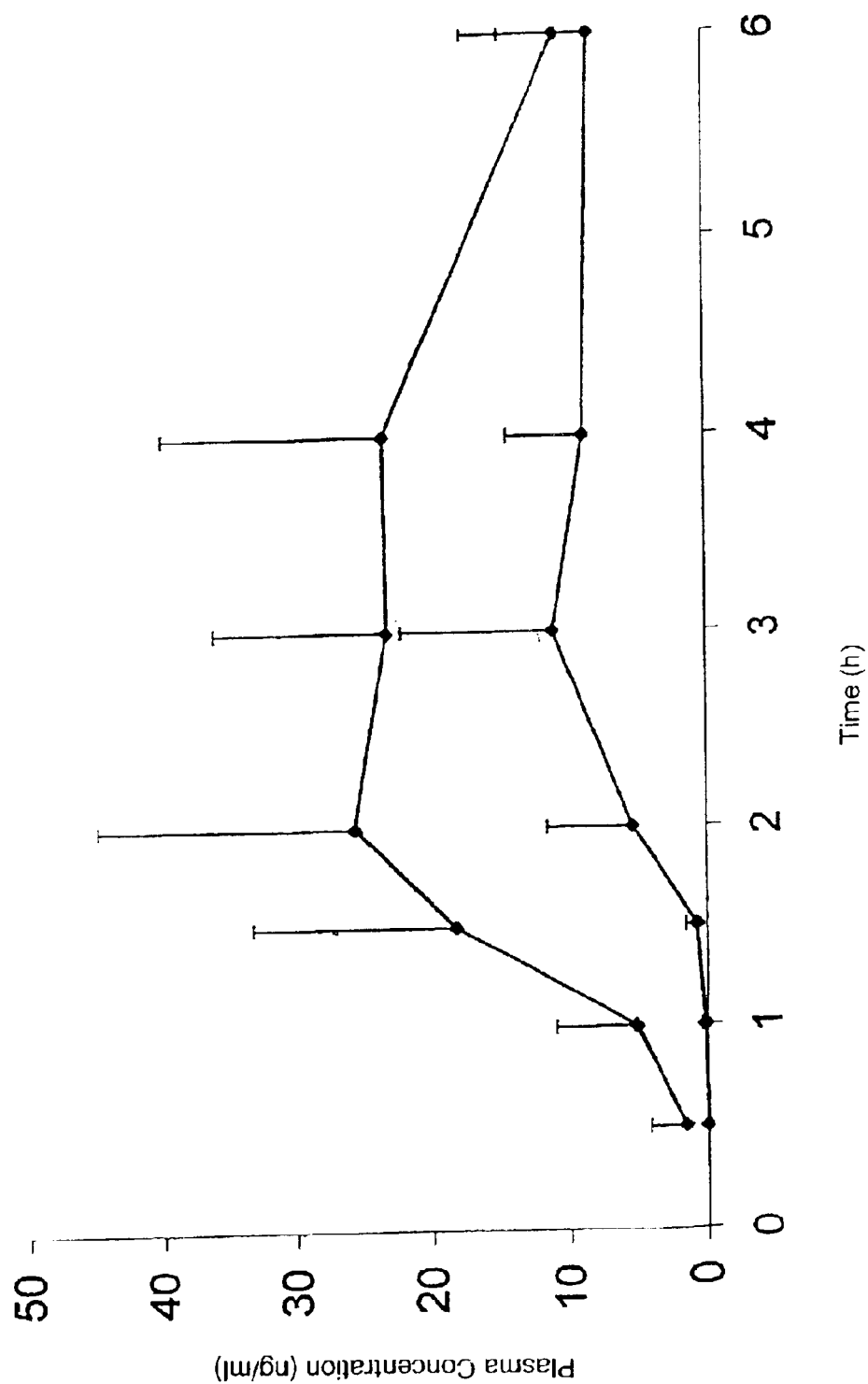
FIG. 10 represents percent average concentration of lercanidipine hydrochloride in dog plasma after administration of crystalline Form (I) and of crystalline Form (II) in an amount of 3 mg/kg, in the form of a hard gelatin capsule. The ordinate indicates the mean value of concentration in plasma and the abscissa indicates time (in minutes).

The profiles referring to the average concentrations of lercanidipine for both forms are shown in FIG. 10. The following Tables 10 and 11 show single values referring to AUC, Tmax, $C_{max}$ and to plasma concentrations.

TABLE 10

Mean values (n = 5) Of $AUC_{0-t}$, $C_{max}$ and $T_{max}$ of lercanidipine hydrochloride (S + R) crystalline Form (I) and crystalline Form (II), in dogs, after oral administration at a dosage of 3 mg/kg.

| Parameter | Dog 1 | Dog 2* | Dog 3 | Dog 4 | Dog 5 | Dog 6 | Mean | SD |
| --- | --- | --- | --- | --- | --- | --- | --- | --- |
| | | | | Form (I) | | | | |
| $AUC_{0-t}$ ng/h/ml | 15.41 | 263.83 | 27.544 | 46.57 | 70.39 | 28.72 | 37.73 | 19.12 |
| $T_{max}$ (h) | 2.00 | 4.00 | 6.00 | 3.00 | 3.00 | 6.00 | 4.00 | 1.67 |
| $C_{max}$ (ng/ml) | 8.29 | 128.87 | 11.62 | 27.17 | 22.58 | 17.83 | 17.50 | 6.91 |
| | | | | Form (II) | | | | |
| $AUC_{0-t}$ ng/h/ml | 54.59 | 119.77 | 75.62 | 173.82 | 142.34 | 61.91 | 104.68 | 43.99 |
| $T_{max}$ (h) | 3.00 | 1.50 | 1.50 | 4.00 | 2.00 | 6.00 | 3.00 | 1.61 |
| $C_{max}$ (ng/ml) | 18.46 | 52.19 | 19.78 | 52.64 | 55.38 | 18.56 | 36.17 | 17.27 |

*not included in the calculation of mean value

TABLE 11

Average concentration in plasma of lercanidipine hydrochloride (S + R) crystalline Form (I) and crystalline Form (II), in dogs, after oral administration at a dosage of 3 mg/kg.

| Time (h) | Dog 1 | Dog 2* | Dog 3 | Dog 4 | Dog 5 | Dog 6 | Mean | SD |
|---|---|---|---|---|---|---|---|---|
| Form (I) | | | | | | | | |
| 0 | 0.00 | 0.00 | 0.00 | 0.00 | 0.00 | 0.00 | 0.00 | 0.00 |
| 0.5 | 0.1 | 0.20 | 0.00 | 0.00 | 0.00 | 0.00 | 0.00 | 0.02 |
| 1 | 0.59 | 0.29 | 0.00 | 0.00 | 0.00 | 0.00 | 0.12 | 0.22 |
| 1.5 | 1.83 | 1.06 | 0.32 | 0.00 | 1.33 | 0.00 | 0.70 | 0.73 |
| 2 | 8.29 | 8.94 | 0.94 | 0.35 | 17.11 | 0.28 | 5.39 | 6.34 |
| 3 | 4.44 | 36.39 | 0.92 | 27.17 | 22.58 | 1.29 | 11.28 | 11.11 |
| 4 | 1.81 | 128.87 | 9.42 | 11.07 | 16.39 | 6.26 | 8.99 | 5.56 |
| 6 | 0.80 | 26.65 | 11.62 | 2.53 | 9.73 | 17.83 | 8.50 | 6.50 |
| Form (II) | | | | | | | | |
| 0 | 0.00 | 0.00 | 0.00 | 0.00 | 0.00 | 0.00 | 0.00 | 0.00 |
| 0.5 | 0.00 | 22.67 | 6.99 | 0.00 | 0.00 | 0.00 | 1.40 | 2.61 |
| 1 | 0.00 | 52.13 | 16.61 | 5.50 | 3.28 | 0.00 | 5.08 | 5.91 |
| 1.5 | 0.23 | 52.19 | 19.78 | 35.43 | 32.69 | 3.49 | 18.32 | 14.88 |
| 2 | 7.63 | 35.45 | 17.81 | 38.10 | 55.38 | 10.19 | 25.82 | 19.23 |
| 3 | 18.46 | 17.43 | 15.80 | 28.36 | 40.57 | 14.10 | 23.46 | 12.56 |
| 4 | 14.83 | 5.17 | 14.10 | 52.64 | 23.66 | 13.24 | 23.69 | 16.26 |
| 6 | 8.05 | 4.50 | 3.62 | 17.46 | 6.76 | 18.56 | 10.89 | 6.82 |

*not included in the calculation of mean value

The formulation containing Form (II) is more bioavailable than the one containing crystalline Form (I) in 5 animals out of 6.

To simplify the comparison, dog 2 was excluded from the evaluation, since after the administration of Form (I) dog 2 shows a plasma AUC of 264 ng/h/ml versus a mean value of 38±19 (SD) of the other 5 dogs. On the other hand, its AUC after administration of Form (I) is similar to that of the other animals, the value being 120 versus 105±44 ng/h/ml.

The bioavailability of lercanidipine hydrochloride (Form (II)), expressed as increase in the AUC of lercanidipine (R+S) obtained after administration of Form (II), is about 3 times higher than that obtained with Form (I). The average profile of plasma concentrations for both crystalline forms is shown in FIG. 10.

The analysis of these results shows that the amount of lercanidipine (S+R) absorbed after administration of crystalline Form (II) is 3 times higher that of Form (I), whereas the absorption speed, expressed as $T_{max}$, is practically unchanged.

Plasma concentrations 6 hours after administration (last sampling time) are similar, the concentrations being of 8.5±6.5 ng/ml after administration of Form (I) and of 10.9±6.8 ng/ml after administration of Form (II).

19b—Man

A study was carried out on 16 healty volunteers to assess the relative bioavailability of lercanidipine hydrochloride Form (I) and Form (II). Form (I) was represented by a tablet of Zanedip$^R$ corresponding to 10 mg of lercanidipine hydrochloride (Reference—R). Form (II) was administered in form of a 10 mg tablet prepared exactly in the same way and with the same composition of Zanedip$^R$ 10 mg, starting from micronized Form (II) having the same particle size of Form I (Test-T). Blood samples were taken at 15 points from time 0 to 24 h post-dosing and plasma concentrations of lercanidipine were determined with a stereoselective analytical method HPLC-MS/MS as described in Example 19a, as validated for man at the same concentration intervals.

The pharmacokinetic parameters obtained are given in the following table

| | Form (I) geom. least square mean | Form (II) geom. least square mean | Point Estimate (T/R) | 90% C.I. |
|---|---|---|---|---|
| $AUC_{0-t}$ (ng · h/mL) | 8.82 | 10.36 | 1.17 | 0.93–1.48 |
| $C_{max}$ (ng/mL) | 3.18 | 3.22 | 1.01 | 0.73–1.42 |
| $t_{max}$ (h) | 1.50* | 2.50* | 0.75** | 0.00–1.25 |
| $C_{max}$/AUC | 0.386^ | 0.329^ | 0.85 | 0.69–1.02 |

*median
**median difference
^least square mean

The obtained results indicated that lercanidipine hdyrochloride Form (II) was not bioequivalent to Form I, with Form (II) obtaining higher plasma levels, that lercanidipine hydrochloride Form (I) has a $t_{max}$ that is shorter than that of Form (II), suggesting its use in immediate release formulations.

Example 20
X-ray Diffraction Studies

Philips PW 1710 and Philips X pert PW 3040 powder diffractometer (Copper Kα radiation) were used, under the following typical conditions: about 5–70 mg sample (without any previous treatment) with application of a slight pressure to obtain a flat surface. Ambient air atmosphere. 0.02° 2θ stepsize, 2 sec step-1, 2–50 2θ.

Figure 11:
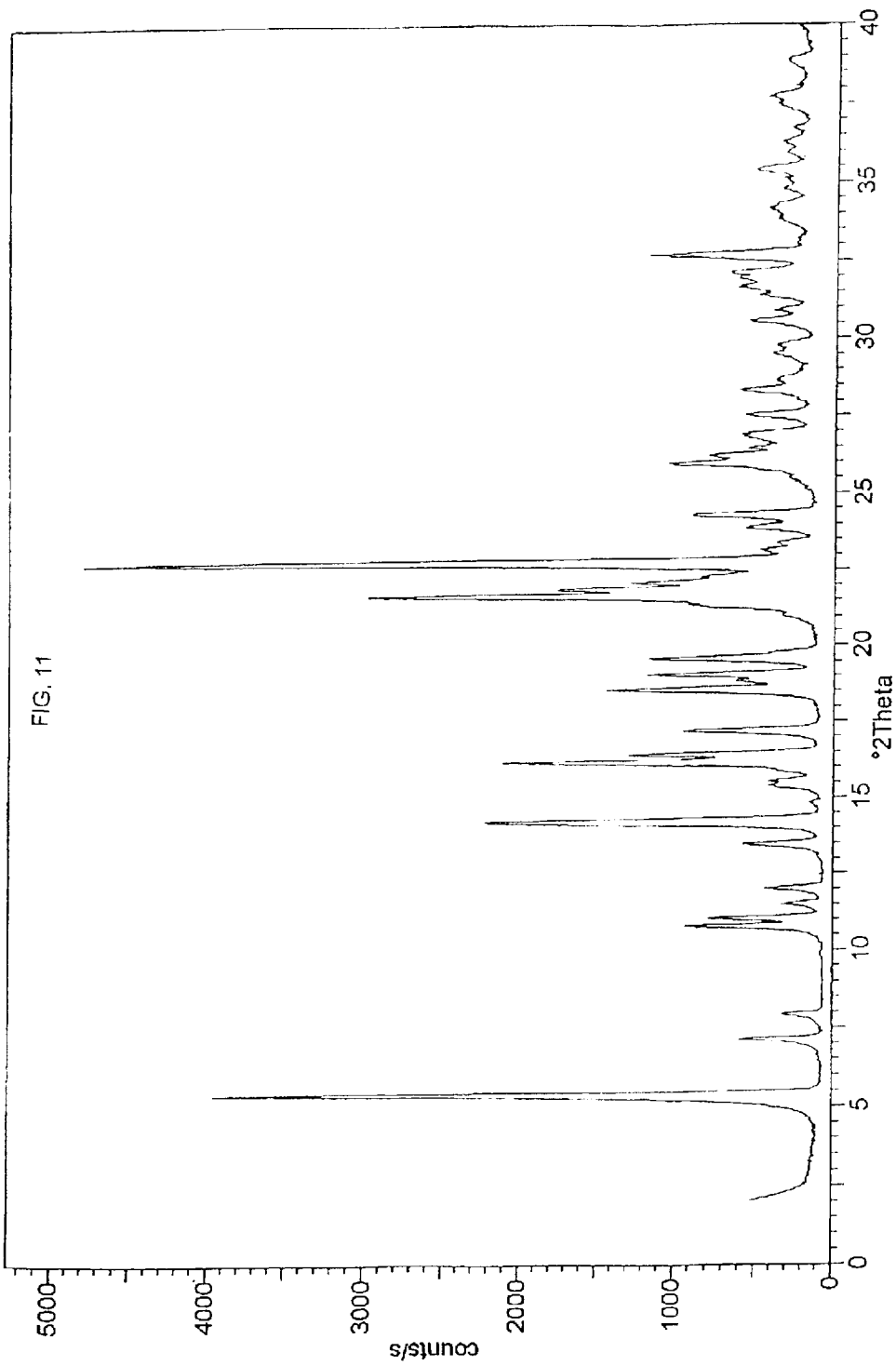
FIGS. 11 and 12 show X-ray diffraction spectra at wavelength Kα of crystalline Forms (I) and (II), respectively. The distances (d) in Å, the (I/Io) ratios and values of 2θ angles of the most significant peaks can be found in Tables 1 and 2 below. The ordinate indicates the number of counts/sec and the abscissa shows the values of 2θ angles.
Figure 12:
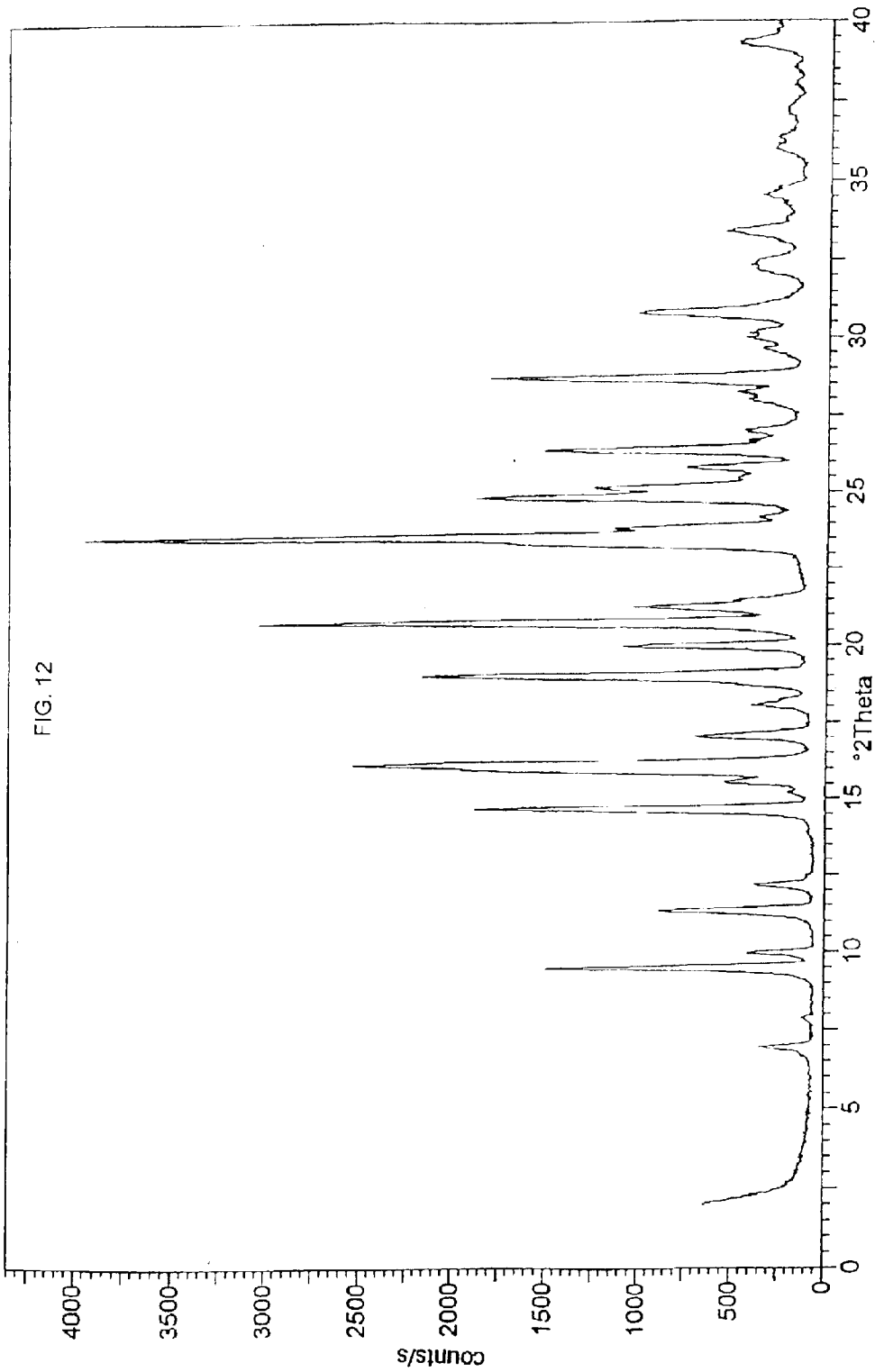

The obtained spectra are given in FIGS. 11 and 12 and the corresponding main peaks are described in Tables 12 and 13. The data are clearly different for new isolated Forms (I) and (II).

TABLE 12

XRD spectrum of lercanidipine hydrochloride Form (I).

| D (Å) | Relative intensity (I/Io) | 2 θ angle |
|---|---|---|
| 16.3 | 83 | 5.4 |
| 6.2 | 47 | 14.2 |
| 4.78 | 29 | 18.6 |
| 4.10 | 63 | 21.7 |
| 4.06 | 36 | 21.9 |
| 3.90 | 100 | 22.8 |

TABLE 13

XRD spectrum of lercanidipine hydrochloride Form (II).

| D (Å) | Relative intensity (I/Io) | 2 θ angle |
|---|---|---|
| 9.3 | 35 | 9.5 |
| 6.0 | 45 | 14.7 |
| 5.49 | 65 | 16.1 |
| 4.65 | 52 | 19.1 |
| 4.27 | 74 | 20.8 |
| 3.81 | 41 | 23.4 |
| 3.77 | 100 | 23.6 |
| 3.58 | 44 | 24.8 |
| 3.54 | 29 | 25.2 |

Example 21
Melting Point Determination of Various Mixtures of Lercanidipine Hydrochloride Crystalline Forms (I) and (II)

The melting points of compositions consisting of known ratios of lercanidipine hydrochloride crystalline Forms (I) and (II) were determined manually. Conditions consisted of using a set point of 177° C. and introducing the capillary into the instrument (Melting Point Apparatus model 535, Büchi

TABLE 14

Melting points of compositions consisting of known ratios of lercanidipine hydrochloride crystalline Forms (I) and (II). Samples in Series A and Series B were heated at a gradient of 1° C./min and 0.5° C./min, respectively. Results are given in °C.

| Sample | Pure Form (I) | Ratio lercanidipine hydrochloride crystalline Form (I):Form (II) | | | | | Pure Form (II) |
|---|---|---|---|---|---|---|---|
| | | 9:1 | 7:3 | 1:1 | 3:7 | 1:9 | |
| Series A | 186.8 | 188.0 | 189.5 | 190.0 | 192.2 | 194.2 | 194.3 |
| Series B | 185.9–186.8 | 184.4–186.1 | 184.5–187.0 | 186.7–187.4 | 186.5–189.4 | 188.7–190.5 | 190.6–192.9 |

U.S. Pat. No. 5,767,136 discloses crystalline lercanidipine hydrochloride as having a melting point of 186–188° C. Table 14 shows that this melting point is exhibited by mixtures of Form (I) and Form(II) in which the ratio of Form (I):Form (II) varies between 9:1 to 3:7. Bianchi et al. (Drugs of the Future, 1987, 12:1113–1115) report a melting point of 186–188° C. (non DSC) for a lercanidipine product they characterize as "crystals". Hence, the melting point of a preparation of lercanidipine hydrochloride is not sufficient by itself to distinguish the particular form or forms present therein, and many mixtures of different compositions have the same melting point range.

Example 22

Micronization of Lercanidipine Hydrochloride

Micronization is carried out by a jet-mill process using a MICRONETTE M300 from the firm NUOVA GUSEO (Villanova sull'Arda-PC-Italy). Parameters are as follows: Injection pressure, 5 Kg/cmq; micronization pressure, 9 Kg/cmq; and cyclone pressure, 2.5 Kg/cmq. Capacity of micronization is 16 Kg/h. Particle size is determined by laser light scattering using a GALAI CIS 1 laser instrument (GALAI, Haifa, Israel). Micronization is performed to obtain an average particle size of D (50%) 2–8 μm and D (90%) <15 μm.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. Isolated lercanidipine crystalline Form (I) which has an X-ray diffraction pattern at wavelength Kα wherein distances, (I/Io) ratios, and 2θ angles of significant peaks are:

| D (Å) | Relative intensity (I/Io) | 2 θ angle |
|---|---|---|
| 16.3 | 83 | 5.4 |
| 6.2 | 47 | 14.2 |
| 4.78 | 29 | 18.6 |
| 4.10 | 63 | 21.7 |
| 4.06 | 36 | 21.9 |
| 3.90 | 100 | 22.8 |

2. The isolated lercanidipine hydrochloride crystalline Form (I) of claim 1, which has the X-ray diffraction pattern as shown in FIG. 11.

3. A method of producing lercanidipine hydrochloride crystalline Form (I), which has an X-ray diffraction pattern, at wavelength Kα, wherein distances, (I/Io) ratios, and 2θ angles of significant peaks are

| D (Å) | Relative intensity (I/Io) | 2 θ angle |
|---|---|---|
| 16.3 | 83 | 5.4 |
| 6.2 | 47 | 14.2 |
| 4.78 | 29 | 18.6 |
| 4.10 | 63 | 21.7 |
| 4.06 | 36 | 21.9 |
| 3.90 | 100 | 22.8 | which comprises:

d) adding a C1–C5 alcohol solvent containing a maximum of 5% water (v/v) to a crude lercanidipine hydrochloride Form and healing under reflux and with stirring to produce a clear solution;

e) cooling the solution of step d) and stirring until the concentration of lercanidipine hydrochloride dissolved in the crystallization solvent is ≦2%; and f) recovering the solid obtained from step e), and drying said solid to produce the lercanidipine hydrochloride crystalline Form (I).

4. The method of claim 3, wherein step f) comprises filtering the solid obtained from step e), washing the solid with isopropanol and re-filtering the solid before drying.

5. The method of claim 3, wherein the alcohol of step d) is selected from the group consisting of isopropanol, ethanol and anhydrous ethanol.

6. The method of claim 3, wherein the crude Form is lercanidipine hydrochloride crude Form (A), lercanidipine hydrochloride crude Form (B) or lercanidipine crude Form (C).

7. The method of claim 3 wherein said step d) further comprises filtering the heated solution.

8. The method of claims 3 wherein said step e) comprises cooling the solution to a temperature between 30 and 40° C.

9. The method of claim 8 wherein said step e) further comprises stirring for a period of time of 12–48 hours.

10. The method of claim 3 wherein said drying in step f) takes place in an oven.

11. A method of producing lercanidipine hydrochloride crystalline Form (I), which has an x-ray diffraction pattern, at wavelength Kα, wherein distances, (I/Io) ratios, and 2θ angles of significant peaks are,

| D (Å) | Relative intensity (I/Io) | 2 θ angle |
|---|---|---|
| 16.3 | 83 | 5.4 |
| 6.2 | 47 | 14.2 |
| 4.78 | 29 | 18.6 |
| 4.10 | 63 | 21.7 |
| 4.06 | 36 | 21.9 |
| 3.90 | 100 | 22.8 | which comprises:

d') providing a mixture of ethanol and lercanidipine hydrochloride, refluxing under stirring and cooling and adding crystalline seeds of Form (I);

e') further cooling the seeded mixture of step d') and stirring until the concentration of lercanidipine hydrochloride dissolved in the crystallization solvent is ≦2%; and f') recovering the solid of step e') to form lercanidipine hydrochloride Form (I).

12. The method of claim 11 wherein the ratio of lercanidipine hydrochloride to volume of solvent in step d') on a weight volume ratio is within the range of about 1:4 to 1:6.

13. The method of claim 12 wherein said ratio is 1:4.

14. The method of claim 11 wherein said step d') further comprises filtering the heated solution.

15. The method of claim 11 wherein cooling in said step d') is to a temperature of 20° C. while stirring.

16. The method of claim 11 wherein cooling in said step e') is to a temperature between 10 and 15° C.

17. The method of claim 11 wherein the drying in said step f') takes place in an oven at 70° C.

18. The method of claim 15 wherein authentic seeds of lercanidipine Form (I) are added at the end of cooling in steps e') and d').

* * * * *

UNITED STATES PATENT AND TRADEMARK OFFICE
CERTIFICATE OF CORRECTION

PATENT NO. : 6,852,737 B2
DATED : February 8, 2005
INVENTOR(S) : Fausto Bonifacio et al.

It is certified that error appears in the above-identified patent and that said Letters Patent is hereby corrected as shown below:

Column 30,
Line 49, please delete "healing" and substitute -- heating --.

Column 32,
Line 22, please insert the following claims:

-- 19. The isolated lercanidipine crystal Form of claim 1 or 2 comprising an average particle size of D (50%) 2-8 $\mu$m and D (90%) < 15 $\mu$m.

20. A lercanidipine hydrochloride crystalline from Form 1 exhibiting essentially the following X-ray diffraction data:

| D (Å) | Relative Intensity (I/Io) |
|-------|---------------------------|
| 16.3  | 83                        |
| 6.2   | 47                        |
| 4.78  | 29                        |
| 4.10  | 63                        |
| 4.06  | 36                        |
| 3.90  | 100                       |

--

Signed and Sealed this

Seventeenth Day of May, 2005

JON W. DUDAS
*Director of the United States Patent and Trademark Office*